United States Patent
Kanamura et al.

(10) Patent No.: US 8,295,922 B2
(45) Date of Patent: Oct. 23, 2012

(54) IONTOPHORESIS DEVICE

(75) Inventors: Kiyoshi Kanamura, Shibuya-ku (JP);
Takehiko Matsumura, Shibuya-ku (JP);
Mizuo Nakayama, Shibuya-ku (JP);
Hidero Akiyama, Shibuya-ku (JP);
Akihiko Matsumura, Shibuya-ku (JP)

(73) Assignee: TTI ellebeau, Inc., Tokyo (JP)

( * ) Notice: Subject to any disclaimer, the term of this patent is extended or adjusted under 35 U.S.C. 154(b) by 1537 days.

(21) Appl. No.: 11/501,176

(22) Filed: Aug. 7, 2006

(65) Prior Publication Data

US 2007/0066931 A1    Mar. 22, 2007

Related U.S. Application Data

(60) Provisional application No. 60/717,874, filed on Sep. 15, 2005.

(30) Foreign Application Priority Data

Aug. 8, 2005  (JP) .................................. 2005-229985

(51) Int. Cl.
*A61N 1/30* (2006.01)
*A61M 31/00* (2006.01)
*A61F 13/00* (2006.01)

(52) U.S. Cl. ........................... 604/20; 604/501; 424/449

(58) Field of Classification Search .................. 424/449; 604/20, 501
See application file for complete search history.

(56) References Cited

U.S. PATENT DOCUMENTS

| | | | |
|---|---|---|---|
| 4,116,889 A | | 9/1978 | Chlanda et al. |
| 4,140,121 A | | 2/1979 | Kuhl et al. |
| 4,519,938 A | * | 5/1985 | Papir ............................ 252/500 |
| 4,585,652 A | * | 4/1986 | Miller et al. ................ 604/891.1 |
| 4,691,718 A | | 9/1987 | Sakuma et al. |
| 4,708,716 A | | 11/1987 | Sibalis |
| 4,725,263 A | | 2/1988 | McNichols et al. ............. 604/20 |
| 4,731,049 A | | 3/1988 | Parsi |
| 4,744,787 A | | 5/1988 | Phipps et al. |
| 4,747,819 A | | 5/1988 | Phipps et al. |
| 4,752,285 A | | 6/1988 | Petelenz et al. |
| 4,915,685 A | | 4/1990 | Petelenz et al. |
| 4,927,408 A | | 5/1990 | Haak et al. |

(Continued)

FOREIGN PATENT DOCUMENTS

CA      2280046       2/1998

(Continued)

OTHER PUBLICATIONS

U.S. Appl. No. 60/717,874, filed Sep. 15, 2005, Kanamura et al.

(Continued)

*Primary Examiner* — Nicholas Lucchesi
*Assistant Examiner* — Ian Holloway
(74) *Attorney, Agent, or Firm* — Seed IP Law Group PLLC

(57) ABSTRACT

An iontophoresis device may be capable of preventing or reducing the generation of gas, or the production of undesirable ions, due to an electrode reaction occurring in an electrode assembly; or the alteration of an active agent due to a chemical reaction upon energization. A doping layer made of a substance such as a conductive polymer that effects an electrochemical reaction due to the doping or de-doping of an ion, may be formed in an electrode in an active electrode assembly or counter electrode assembly of an iontophoresis device.

30 Claims, 14 Drawing Sheets

U.S. PATENT DOCUMENTS

| | | | |
|---|---|---|---|
| 4,931,046 A | 6/1990 | Newman | |
| 4,940,456 A | 7/1990 | Sibalis et al. | 604/20 |
| 4,944,296 A | 7/1990 | Suyama | |
| 5,057,072 A | 10/1991 | Phipps | |
| 5,080,646 A | 1/1992 | Theeuwes et al. | |
| 5,084,006 A | 1/1992 | Lew et al. | |
| 5,135,477 A | 8/1992 | Untereker et al. | |
| 5,147,296 A | 9/1992 | Theeuwes et al. | |
| 5,162,043 A | 11/1992 | Lew et al. | |
| 5,167,616 A | 12/1992 | Haak et al. | |
| 5,169,383 A | 12/1992 | Gyory et al. | |
| 5,203,768 A | 4/1993 | Haak et al. | |
| 5,206,756 A * | 4/1993 | Cheshire | 359/270 |
| 5,224,927 A | 7/1993 | Tapper | 604/20 |
| 5,238,613 A | 8/1993 | Anderson | |
| 5,244,557 A * | 9/1993 | Defendini et al. | 204/192.29 |
| 5,246,417 A | 9/1993 | Haak et al. | |
| 5,298,017 A | 3/1994 | Theeuwes et al. | |
| 5,310,404 A | 5/1994 | Gyory et al. | |
| 5,312,326 A | 5/1994 | Myers et al. | |
| 5,320,597 A | 6/1994 | Sage, Jr. et al. | |
| 5,322,502 A | 6/1994 | Theeuwes et al. | |
| 5,326,341 A | 7/1994 | Lew et al. | |
| 5,374,241 A | 12/1994 | Lloyd et al. | |
| 5,380,271 A | 1/1995 | Gyory | |
| 5,380,272 A | 1/1995 | Gross | |
| 5,385,543 A | 1/1995 | Haak et al. | |
| 5,405,317 A | 4/1995 | Myers et al. | |
| 5,425,703 A | 6/1995 | Feiring | |
| 5,445,606 A | 8/1995 | Haak et al. | |
| 5,464,387 A | 11/1995 | Haak et al. | |
| 5,543,098 A | 8/1996 | Myers et al. | |
| 5,551,953 A | 9/1996 | Lattin et al. | |
| 5,558,633 A | 9/1996 | Phipps et al. | |
| 5,573,503 A | 11/1996 | Untereker et al. | |
| 5,573,668 A | 11/1996 | Grosh et al. | |
| 5,582,587 A | 12/1996 | Gyory et al. | |
| 5,637,084 A | 6/1997 | Kontturi et al. | |
| 5,647,844 A | 7/1997 | Haak et al. | 604/20 |
| 5,723,130 A | 3/1998 | Hancock et al. | |
| 5,725,817 A | 3/1998 | Milder | |
| 5,738,647 A | 4/1998 | Bernhard et al. | 604/20 |
| 5,817,044 A | 10/1998 | Evers et al. | 604/20 |
| 5,840,056 A | 11/1998 | Atanasoska | |
| 5,840,339 A | 11/1998 | Kunin | 424/489 |
| 5,919,155 A | 7/1999 | Lattin et al. | 604/20 |
| 5,928,185 A | 7/1999 | Muller et al. | 604/20 |
| 5,976,101 A | 11/1999 | Sibalis | |
| 5,991,655 A | 11/1999 | Gross et al. | 604/20 |
| 5,993,435 A | 11/1999 | Haak et al. | |
| 5,995,869 A | 11/1999 | Cormier et al. | |
| 6,006,130 A | 12/1999 | Higo et al. | |
| 6,032,073 A | 2/2000 | Effenhauser | |
| 6,047,208 A | 4/2000 | Flower | |
| 6,049,733 A | 4/2000 | Phipps et al. | |
| 6,064,908 A | 5/2000 | Muller et al. | |
| 6,086,572 A | 7/2000 | Johnson et al. | |
| 6,103,078 A | 8/2000 | Hitchems et al. | |
| 6,109,852 A | 8/2000 | Shahinpoor et al. | |
| 6,167,302 A | 12/2000 | Millot | |
| 6,169,920 B1 | 1/2001 | Haak et al. | |
| 6,195,582 B1 | 2/2001 | Scott | |
| 6,223,075 B1 | 4/2001 | Beck et al. | 604/20 |
| 6,228,206 B1 | 5/2001 | Herman et al. | |
| 6,258,276 B1 | 7/2001 | Mika et al. | |
| 6,289,241 B1 | 9/2001 | Phipps | 604/20 |
| 6,314,317 B1 | 11/2001 | Willis | |
| 6,329,488 B1 | 12/2001 | Terry et al. | |
| 6,330,471 B1 | 12/2001 | Higo et al. | |
| 6,335,266 B1 * | 1/2002 | Kitahara et al. | 438/475 |
| 6,336,049 B1 | 1/2002 | Kinbara et al. | |
| 6,377,847 B1 | 4/2002 | Keusch et al. | |
| 6,405,875 B1 | 6/2002 | Cutler | |
| 6,454,941 B1 | 9/2002 | Cutler et al. | |
| 6,462,935 B1 | 10/2002 | Shiue et al. | |
| 6,468,657 B1 | 10/2002 | Hou et al. | 428/403 |
| 6,477,410 B1 | 11/2002 | Henley et al. | |
| 6,496,727 B1 | 12/2002 | Bernhard et al. | |
| 6,497,887 B1 | 12/2002 | Zecchino et al. | |
| 6,505,069 B2 | 1/2003 | Scott et al. | |
| 6,532,386 B2 | 3/2003 | Sun et al. | 604/20 |
| 6,553,255 B1 | 4/2003 | Miller et al. | |
| 6,560,483 B1 | 5/2003 | Kumar et al. | |
| 6,584,349 B1 | 6/2003 | Sage, Jr. et al. | |
| 6,597,947 B1 | 7/2003 | Inoue et al. | |
| 6,635,045 B2 | 10/2003 | Keusch et al. | |
| 6,654,635 B1 | 11/2003 | Koga et al. | |
| 6,678,554 B1 | 1/2004 | Sun et al. | |
| 6,692,456 B1 | 2/2004 | Eppstein et al. | 604/22 |
| 6,708,050 B2 | 3/2004 | Carim | |
| 6,725,090 B1 | 4/2004 | Lattin et al. | 604/20 |
| 6,731,977 B2 | 5/2004 | Beck | |
| 6,743,015 B2 | 6/2004 | Magnani | |
| 6,743,432 B2 | 6/2004 | Yanai et al. | 424/400 |
| 6,745,071 B1 | 6/2004 | Anderson et al. | |
| 6,775,569 B2 | 8/2004 | Mori et al. | 604/20 |
| 6,855,441 B1 | 2/2005 | Levanon | |
| 6,862,473 B2 | 3/2005 | Keusch et al. | |
| 6,915,159 B1 | 7/2005 | Kuribayashi et al. | |
| 6,918,901 B1 | 7/2005 | Theeuwes et al. | 604/500 |
| 6,975,902 B2 | 12/2005 | Phipps et al. | |
| 7,018,370 B2 | 3/2006 | Southam et al. | |
| 7,054,682 B2 * | 5/2006 | Young et al. | 604/20 |
| 7,127,285 B2 * | 10/2006 | Henley et al. | 604/20 |
| 7,392,080 B2 | 6/2008 | Eppstein et al. | 604/20 |
| 7,398,121 B2 * | 7/2008 | Matsumura et al. | 604/20 |
| 2002/0022795 A1 | 2/2002 | Reynolds et al. | |
| 2002/0099320 A1 | 7/2002 | Beck | |
| 2002/0188241 A1 | 12/2002 | Morris et al. | 604/20 |
| 2003/0052015 A1 * | 3/2003 | Becker et al. | 205/414 |
| 2003/0088205 A1 | 5/2003 | Chandrasekaran et al. | 604/20 |
| 2003/0168404 A1 | 9/2003 | Mika et al. | |
| 2003/0208152 A1 | 11/2003 | Avrahami et al. | 604/20 |
| 2004/0071765 A1 | 4/2004 | Adachi et al. | |
| 2004/0105881 A1 | 6/2004 | Cevc et al. | |
| 2004/0138609 A1 | 7/2004 | Fukuta et al. | 604/20 |
| 2004/0143210 A1 | 7/2004 | Shevlin | |
| 2004/0167459 A1 | 8/2004 | Higuchi et al. | |
| 2004/0176803 A1 | 9/2004 | Whelan et al. | 607/2 |
| 2004/0176805 A1 | 9/2004 | Whelan et al. | 607/2 |
| 2004/0225253 A1 | 11/2004 | Shevlin | 604/20 |
| 2005/0011826 A1 | 1/2005 | Childs et al. | |
| 2005/0070840 A1 | 3/2005 | Matsumura et al. | |
| 2005/0131336 A1 | 6/2005 | Mori et al. | |
| 2005/0143686 A1 | 6/2005 | Shevlin | 604/20 |
| 2005/0148996 A1 | 7/2005 | Sun et al. | |
| 2005/0169976 A1 | 8/2005 | Mori et al. | |
| 2005/0267440 A1 | 12/2005 | Herman et al. | 604/501 |
| 2005/0287201 A1 | 12/2005 | Till et al. | 424/450 |
| 2006/0009730 A2 | 1/2006 | Shevlin | 604/20 |
| 2006/0083962 A1 | 4/2006 | Takekawa et al. | 429/13 |
| 2006/0095001 A1 | 5/2006 | Matsumura et al. | |
| 2006/0116628 A1 | 6/2006 | Matsumura et al. | |
| 2006/0129085 A1 | 6/2006 | Tanioka et al. | |
| 2006/0135906 A1 | 6/2006 | Matsumura et al. | |
| 2006/0173401 A1 | 8/2006 | Tanioka et al. | |
| 2006/0198879 A1 | 9/2006 | Fukuta et al. | |
| 2006/0211980 A1 | 9/2006 | Cormier et al. | |
| 2006/0217654 A1 | 9/2006 | Matsumura et al. | |
| 2006/0247364 A1 * | 11/2006 | Murray et al. | 524/495 |
| 2006/0260955 A1 | 11/2006 | Sasaki et al. | 205/759 |
| 2006/0276742 A1 | 12/2006 | Matsumura et al. | |
| 2007/0021711 A1 | 1/2007 | Matsumura et al. | |
| 2007/0027426 A1 | 2/2007 | Matsumura et al. | |
| 2007/0031730 A1 | 2/2007 | Kawakami et al. | 429/218.1 |
| 2007/0048362 A1 | 3/2007 | Nakayama et al. | |
| 2007/0060859 A1 | 3/2007 | Kanamura et al. | |
| 2007/0060860 A1 | 3/2007 | Nakayama et al. | |
| 2007/0060862 A1 | 3/2007 | Sun et al. | 604/20 |
| 2007/0066930 A1 | 3/2007 | Tanioka et al. | |
| 2007/0066932 A1 | 3/2007 | Akiyama et al. | |
| 2007/0071807 A1 | 3/2007 | Akiyama et al. | |
| 2007/0073212 A1 | 3/2007 | Matsumura | |
| 2007/0074590 A1 | 4/2007 | Smith | |
| 2007/0078374 A1 | 4/2007 | Smith | |
| 2007/0078375 A1 | 4/2007 | Smith | |
| 2007/0078376 A1 | 4/2007 | Smith | |

| | | | |
|---|---|---|---|
| 2007/0083147 A1 | 4/2007 | Smith | |
| 2007/0083186 A1 | 4/2007 | Carter et al. | |
| 2007/0088332 A1 | 4/2007 | Akiyama et al. | |
| 2007/0093787 A1 | 4/2007 | Smith | |
| 2007/0100274 A1 | 5/2007 | Young et al. | 604/20 |
| 2007/0112294 A1 | 5/2007 | Akiyama et al. | |
| 2007/0135754 A1 | 6/2007 | Akiyama et al. | |
| 2007/0139862 A1* | 6/2007 | Tateishi et al. | 361/502 |
| 2007/0197955 A1 | 8/2007 | Akiyama et al. | |
| 2007/0213652 A1 | 9/2007 | Carter | |
| 2007/0232983 A1 | 10/2007 | Smith | |
| 2008/0033338 A1 | 2/2008 | Smith | |
| 2008/0033398 A1 | 2/2008 | Reed et al. | |
| 2008/0154178 A1 | 6/2008 | Carter et al. | 604/20 |
| 2008/0213646 A1 | 9/2008 | Takekawa et al. | 429/33 |
| 2008/0217586 A1* | 9/2008 | Maruyama et al. | 252/500 |

FOREIGN PATENT DOCUMENTS

| | | |
|---|---|---|
| EP | 0 097 436 | 1/1984 |
| EP | 0411146 | 2/1991 |
| EP | 0 504 715 | 9/1992 |
| EP | 0 824 003 | 2/1998 |
| EP | 0 931 564 A1 | 7/1999 |
| EP | 1 440 707 | 7/2004 |
| EP | 1 566 197 | 8/2005 |
| GB | 2 265 088 | 9/1993 |
| JP | 52-151720 | 12/1977 |
| JP | 60-35936 | 2/1985 |
| JP | 63-35266 | 2/1988 |
| JP | 03-094771 | 4/1991 |
| JP | 3-504343 | 9/1991 |
| JP | 04-297277 | 10/1992 |
| JP | 05-220385 | 8/1993 |
| JP | 7-504110 | 5/1995 |
| JP | 8-503875 | 4/1996 |
| JP | 09-201420 | 8/1997 |
| JP | 9-248344 | 9/1997 |
| JP | 2792661 | 6/1998 |
| JP | 2-801083 | 7/1998 |
| JP | 2845509 | 10/1998 |
| JP | 2901348 | 3/1999 |
| JP | 11-123246 | 5/1999 |
| JP | 11-239621 | 9/1999 |
| JP | 3040517 | 3/2000 |
| JP | 2000-229128 | 8/2000 |
| JP | 2000-229129 | 8/2000 |
| JP | 2000-237326 | 9/2000 |
| JP | 2000-237327 | 9/2000 |
| JP | 2000-237328 | 9/2000 |
| JP | 2000-237329 | 9/2000 |
| JP | 2000-288097 | 10/2000 |
| JP | 2000-288098 | 10/2000 |
| JP | 2000-316991 | 11/2000 |
| JP | 2001-70459 | 3/2001 |
| JP | 2001-505091 | 4/2001 |
| JP | 2002-233584 | 8/2002 |
| JP | 2002-536133 | 10/2002 |
| JP | 2003-299743 | 10/2003 |
| JP | 2004-188188 | 7/2004 |
| JP | 2004-202057 | 7/2004 |
| JP | 2004-292438 | 10/2004 |
| JP | 2004-317317 | 10/2004 |
| JP | 2004-357313 | 12/2004 |
| JP | 2005-222892 | 8/2005 |
| JP | 2006-149891 | 6/2006 |
| JP | 2006-212194 | 8/2006 |
| JP | 2007-037640 | 2/2007 |
| JP | 2007-050136 | 3/2007 |
| JP | 2007-075327 | 3/2007 |
| WO | 90/03825 | 4/1990 |
| WO | 90/04433 | 5/1990 |
| WO | 90/08571 | 8/1990 |
| WO | 91/16943 | 11/1991 |
| WO | 93/18727 | 9/1993 |
| WO | 94/22528 | 10/1994 |
| WO | 95/35132 | 12/1995 |
| WO | 97/47353 | 12/1997 |
| WO | WO 97/48444 | 12/1997 |
| WO | 98/35722 | 8/1998 |
| WO | 99/38565 | 8/1999 |
| WO | 00/47274 | 8/2000 |
| WO | 00/66216 | 11/2000 |
| WO | WO 01/39830 | 6/2001 |
| WO | 03/008078 | 1/2003 |
| WO | 03/037425 | 5/2003 |
| WO | 03/061758 | 7/2003 |
| WO | WO 2004/028626 | 4/2004 |
| WO | 2004/073843 | 9/2004 |
| WO | WO 2005/120631 | 12/2005 |
| WO | 2006/046703 | 5/2006 |
| WO | 2006/062108 | 6/2006 |
| WO | WO 2008/027218 | 3/2008 |

OTHER PUBLICATIONS

U.S. Appl. No. 11/541,399, filed Sep. 29, 2006, Carter.

Ito, et al., "Iontophoresis in Okeru Ion Kokanmake no in Vitro Koka," Medicine and Biology, 147(3): pp. 41-46, 2003. (+ 13 p. English Translation).

JIS (Japanese Industrial Standards), Testing Methods for Bubble Point of Membrane Filters, K3832-1990, 11 pages.

Kobayashi, Y., "Shin Zairyou Series Dodensei Koubunshi No Saishin Ouyou Gijutsu," CMC Publishing Co., Ltd., Jul. 2004.

Ogata, N., "Dodensei Kobnushi," (Electrically Conductive High Molecular Compounds), Kodansha Scientific, 1990.

Cabovska, "Investigations of Separation Mechanisms in Capillary Electrophoresis and High Performance Liquid Chromatography," Proquest, UMI No. 3120882, 2004.

Kalia, Y., et al., "Iontophoretic Drug Delivery," *Advanced Drug Delivery Reviews*, 56:619-658, 2004.

\* cited by examiner

IONTOPHORESIS DEVICE

BACKGROUND

1. Field

The present disclosure generally relates to the field of iontophoresis, and in particular, to an iontophoresis device capable of preventing or suppressing an undesirable electrode reaction in an electrode assembly.

2. Description of the Related Art

Iontophoresis involves electrically driving an active agent that has dissociated into positive or negative ions in solution by using a voltage to transdermally transfer the active agent into a subject, and has advantages such as reduced patient burden and excellent controllability of the amount of the active agent to be administered.

FIG. 9 is an explanatory view that shows a basic configuration of an iontophoresis device.

The iontophoresis device of FIG. 9 comprises: an active electrode assembly 110 having an electrode 111 and an active agent solution reservoir 114 that holds a solution of an active agent dissociated into positive or negative active agent ions (active agent solution); a counter electrode assembly 120 having an electrode 121 and an electrolyte solution reservoir 122 that holds an electrolyte solution; and an electric power source 130 including two terminals connected to the electrodes 111 and 121. An electrical potential or voltage having the same polarity as that of active agent ions is applied to the electrode 111 and an electrical potential or voltage having a polarity opposite to that of the active agent ion is applied to the electrode 121 in a state where the active agent solution reservoir 114 and the electrolyte solution reservoir 122 are brought into contact a biological interface of a subject. The active agent ions are thus administered to the subject.

Problems that may occur in such an iontophoresis device include a variety of electrode reactions occurring in the electrode assemblies 110 and 120.

For example, when using a cationic drug that dissociates into positive active agent ions, hydrogen ions or oxygen gas may be generated at the electrode 111 and hydroxide ions or hydrogen gas may be generated at the electrode 121 due to the electrolysis of water. In addition, the active agent causes a chemical reaction near the electrode 111 to change depending upon the kind of the active agent and the energization conditions. Furthermore, when the active agent solution reservoir 114 contains chlorine ions, a chlorine gas or hypochlorous acid may be generated.

Similarly, when using an anionic drug that dissociates into negative active agent ions, hydroxide ions or a hydrogen gas may be generated at the electrode 111 and hydrogen ions or an oxygen gas may be generated at the electrode 121 due to the electrolysis of water. In addition, the active agent causes a chemical reaction near the electrode 111 to change depending upon the kind of the active agent and the energization conditions. Furthermore, when the electrolyte solution reservoir 122 contains chlorine ions, a chlorine gas or hypochlorous acid may be generated.

Energization from the electrode 111 or 121 to the active agent solution or the electrolyte solution may be inhibited when a gas as described above is generated in the electrode assembly 110 or 120. When hydrogen ions, hydroxide ions, or hypochlorous acid are generated in the electrode assembly 110 or 120, they may transfer to a biological interface and have a detrimental effect on a subject. In addition, the alteration of an active agent may cause undesirable conditions such as the inability to obtain an initial drug effect and the production of a toxic substance.

U.S. Pat. No. 4,744,787 discloses, as an iontophoresis device capable of solving such problems as described above, an iontophoresis device in which a silver electrode is used as an anode and a silver chloride electrode is used as a cathode.

In the disclosed device, a reaction preferentially occurs where silver in the anode is oxidized by energization to become insoluble silver chloride, while silver chloride is reduced at the cathode to become metallic silver. As a result, the generation of various gases and the production of various ions due to such electrode reactions as described above can be suppressed.

However, it is difficult to prevent the dissolution of the silver electrode during storage of the iontophoresis device. In particular, when the device is intended for use administering a cationic drug, the amount of applicable drug types is extremely limited. In addition, morphological change upon production of silver chloride from the silver electrode is large. Therefore, special consideration must be given in order to prevent such morphological change from affecting the properties of the device. As a result, a problem may arise in that a severe restriction is imposed on the configuration of the device (for example, it may be impossible to adopt a laminate structure). Furthermore, the iontophoresis device is unable to solve the problem of the alteration of the active agent upon energization.

JP 3040517 B discloses an iontophoresis device shown in FIG. 10 as another iontophoresis device capable of solving the problems described above.

Referring to FIG. 10, the iontophoresis device comprises: an active electrode assembly 210 including an electrode 211, an electrolyte solution reservoir 212 holding an electrolyte solution in contact the electrode 211, an ion exchange membrane 213 of a second polarity, the ion exchange membrane 213 being placed on the front surface side of the electrolyte solution reservoir 212, an active agent solution reservoir 214 holding an active agent solution containing active agent ions of a first polarity, the active agent solution reservoir 214 being placed on the front surface side of the ion exchange membrane 213, and an ion exchange membrane 215 of the first polarity, the ion exchange membrane 215 being placed on the front surface side of the active agent solution reservoir 214; and a counter electrode assembly 220 and an electric power source 230 similar to those shown in FIG. 9.

In the iontophoresis device, the electrolyte solution and the active agent solution are partitioned by the second ion exchange membrane 213 of the second polarity. As a result, the composition of the electrolyte solution can be selected independently of the active agent solution. An electrolyte solution that does not contain chlorine ions can thus be used. In addition, the selection of an electrolyte having a lower oxidation or reduction potential than the electrolysis of water as the electrolyte in the electrolyte solution can suppress the production of oxygen gas, hydrogen gas, hydrogen ions, and hydroxide ions resulting from the electrolysis of water. Alternatively, the use of a buffer electrolyte solution into which a plurality of electrolytes are dissolved may suppress changes in pH due to the production of hydrogen ions or hydroxide ions. Furthermore, the transfer of active agent ions to the electrolyte solution reservoir is blocked by the second ion exchange membrane, thus solving a problem where the active agent alters due to a chemical reaction occurring when the device is turned on.

However, the iontophoresis device disclosed in JP 3040517 B comprises a large number of members, and the electrolyte solution reservoir 212 and the active agent solution reservoir 214 must each be handled in a wet state (a state with high water content). Therefore, a problem arises in that automated device production and mass production of the device may be difficult, and may not result in production cost reductions.

Other references considered include "KS Kagaku Senmonsho Dodensei Kobunshi" edited by Naoya Ogata, Kodansha, published January, 1990, and "Shin Zairyou series Dodensei Koubunshi no Saishin Ouyou Gijutsu" written by Yukuo Kobayashi, CMC Publishing CO., LTD., published July, 2004

BRIEF SUMMARY OF THE INVENTION

In one aspect, the present disclosure is directed to an iontophoresis device capable of preventing or suppressing the generation of oxygen gas, chlorine gas, or hydrogen gas in an electrode assembly.

In another aspect, the present disclosure is directed to an iontophoresis device capable of preventing or suppressing the generation of hydrogen ions, hydroxide ions, or hypochlorous acid in an electrode assembly.

In a further aspect, the present disclosure is directed to an iontophoresis device capable of preventing or suppressing the changes to an active agent due to a chemical reaction upon energization.

In an additional aspect, the present disclosure is directed to an iontophoresis device which is capable of preventing or suppressing the generation of gas or ions, as described above, or is capable of preventing or suppressing changes in an active agent, and which does not cause a large morphological change to an electrode due to energization.

In yet another aspect, the present disclosure is directed to an iontophoresis device which is capable of preventing or suppressing the generation of gas or ions, as described above, or is capable of preventing or suppressing changes in an active agent, and which has a simplified structure.

In a yet further aspect, the present disclosure is directed to an iontophoresis device which is capable of preventing or suppressing the generation of gas or ions, as described above, or is capable of preventing or suppressing changes in an active agent. In addition, automated and/or mass production of the device may be easily performed.

In one more aspect, the present disclosure is directed to an iontophoresis device which is capable of preventing or suppressing the generation of gas or ions, as described above, or is capable of preventing or suppressing changes in an active agent, and which may have lower production costs.

In still one more aspect, the present disclosure is directed to an iontophoresis device comprising at least one electrode assembly including an electrode with a doping layer made of a substance effecting an electrochemical reaction due to the doping or de-doping of an ion (hereinafter, an electrode having a doping layer may be referred to as a "doping electrode").

Therefore, energization from an electric power source to an electrolyte solution or an active agent solution may be mostly or entirely caused by doping an ion into, or de-doping an ion from, a doping layer. As a result, an electrode reaction that may tend to generate a gas such as oxygen, chlorine, or hydrogen, or undesirable ions such as hydrogen ions, hydroxide ions, or hypochlorous acid may be prevented or at least reduced.

Effecting an electrochemical reaction due to the doping of an ion refers to the fact that, when positive or negative charge is given to a doping layer, the doping layer thus formed captures ions having the opposite charge as that of an electrolyte solution or active agent solution in contact with the doping layer. The layer is doped with the ion (the ion binds to a substance constituting the doping layer), so the given charge is compensated. Effecting an electrochemical reaction due to the de-doping of an ion refers to the fact that, when positive charge is given to a positively doped layer, positive ions are de-doped and released from the doping layer, thus compensating the given charge. Alternatively, when negative charge is given to a negatively doped layer, negative ions are de-doped and released from the doping layer, thus compensating the given charge.

Conductive polymers such as polyaniline, polypyrrole, polythiophene, polyacetylene, or a derivative or a mixture thereof, are typically used in the doping layer. Of those, polyaniline may be most preferred. "KS Kagaku Senmonsho Dodensei Kobunshi" edited by Naoya Ogata, Kodansha, published on January, 1990, and "Shin Zairyou series Dodensei Koubunshi no Saishin Ouyou Gijutsu" written by Yukuo Kobayashi, CMC Publishing CO., LTD., published on July, 2004, both incorporated herein by reference in their entirety, detail derivatives of polyaniline, polypyrrole, polythiophene, or polyacetylene that can be used for the doping layer in accordance with the teachings herein.

Various methods are known for producing conductive polymers, and various methods are known for forming a conductive polymer into a film. Examples of such methods include: subjecting a powder-like conductive polymer chemically synthesized by means of an oxidation polymerization method to compression molding; bringing a conductive polymer into an ink state by means of a polar organic solvent such as N-methylpyrrolidone, molding the ink-like polymer, and removing the solvent; and immersing an appropriate conductive base material in a solution of a monomer for producing a conductive polymer and performing electrolytic polymerization to form a conductive polymer layer on the base material. The doping layer may be formed by means of any one of those methods.

The entirety of the doping layer may include only the conductive polymer, or it may also include additional components other than the conductive polymer. For example, a suitable woven or non-woven fabric impregnated with the conductive polymer may be used in order to impart mechanical strength against tears or breakage. The conductive polymer and an appropriate polymer binder may also be blended together. Alternatively, in order to improve the conductivity of the conductive polymer, the conductive polymer may be blended with a conductive filler such as carbon.

As described below, the conductive polymer may be doped with active agent ions to be administered to a subject, or with an ion substituting for active agent ions with which the first ion exchange membrane is doped. In addition, the conductive polymer may be doped with an ion as an electron acceptor or an electron donor for the purpose of improving the conductivity of the conductive polymer.

Examples of materials that can be used in the doping layer include carbon materials such as graphite.

An electrode assembly having the doping electrode can be directly used as a counter electrode assembly. The electrode assembly having the doping electrode can be used also as an active electrode assembly by doping the doping layer with active agent ions before use.

That is, energization may be performed by applying an electrical potential or voltage having the polarity opposite to that of active agent ions to the doping electrode in a state where the doping layer is immersed in an active agent solution containing the active agent ion at an appropriate, whereby the doping layer can be doped with the active agent ion.

In addition, the active agent ion may be administered to a subject by applying an electrical potential or voltage having the same polarity as that of the active agent ion to the doping electrode in a state where the doping layer doped with the active agent ion is brought into contact a biological interface of the subject.

In this case, energization from the doping electrode to the subject is entirely or partially caused by the de-doping of the active agent ion from the doping layer to transfer to the subject. As a result, the gas or undesirable ion generation may be prevented or at least reduced.

Furthermore, the doping layer doped with the active agent ion functions as an ion exchange membrane of the same polarity as that of the active agent ion. That is, doping the doping layer with a positive active agent ion imparts an ion exchange function to the doping layer, thus permitting the passage of positive ions and blocking the passage of negative ions. Similarly, doping the doping layer with a negative active agent ion imparts an ion exchange function to the doping layer, permitting the passage of negative ions and blocking the passage of positive ions.

Therefore, upon administration of the active agent ion to a subject, the transfer of a subject counter ion (an ion present on the surface of the subject or in the subject, the ion being charged to the polarity opposite to that of the active agent ion) to the doping layer may be blocked, whereby the amount of a current consumed can be reduced, and the efficiency of administration of an active agent can be increased.

The doping of the doping layer with the active agent ion when the electrode assembly having the doping electrode is used as an active electrode assembly as described above may be performed at any time from production of the iontophoresis device or the active electrode assembly through to a time immediately before use (the administration of an active agent to a subject).

An iontophoresis device typically comprises an active electrode assembly holding an active agent to be administered to a subject and a counter electrode assembly serving as a counter electrode of the active electrode assembly. One, or preferably both, of the active electrode assembly or the counter electrode assembly may be an electrode assembly having a doping electrode.

An active agent to be administered to a subject may be held by each of two electrode assemblies to be connected to both polarities of an electric power source (in this case, each of both electrode assemblies serves as an active electrode assembly and a counter electrode assembly), or multiple electrode assemblies may be connected to each polarity of an electric power source, depending upon the agent or agents to be delivered. In this case at least one of the electrode assemblies may include a doping electrode. Alternatively, preferably all of the electrode assemblies include a doping electrode.

An electrode assembly that comprises a doping electrode may have a simple structure. Automated production and mass production of an iontophoresis device that comprises one or more doping electrodes may thus be easily performed. Further, production costs may be significantly reduced.

The electrode assembly may further include an active agent solution reservoir holding an active agent solution containing active agent ions of the first polarity, the active agent solution reservoir being placed on the front surface side of the doping layer.

Such an electrode assembly may be used as an active electrode assembly in an iontophoresis device. Active agent ions in the active agent solution reservoir may be administered to a subject by applying an electrical potential or voltage of the first polarity to the doping electrode in a state where the active agent solution reservoir is brought into contact a biological interface of the subject.

In this case, the doping layer captures an ion of a second polarity from the active agent solution reservoir, and the layer is doped with the ion, whereby energization from the doping electrode to the active agent solution reservoir occurs. Therefore, the generation of gases and undesirable ions can be suppressed.

The doping layer can be doped with an ion of the first polarity in advance. In this case, energization from the doping electrode to the active agent solution reservoir is caused by the doping with an ion of the second polarity in the active agent solution reservoir and the de-doping of an ion of the first polarity from the doping layer. It should be noted that the same may also hold true other embodiments.

The doping layer can be doped with an ion of the first polarity through energization as a result of applying an electrical potential or voltage of the second polarity to the doping electrode in a state where the doping layer is immersed in an electrolyte solution containing an appropriate concentration of the ion of the first polarity.

In some embodiments, the electrode assembly preferably further comprises a first ion exchange membrane of the first polarity placed on the front surface side of the active agent solution reservoir.

The active agent ion in the active agent solution reservoir may then be administered to a subject through the first ion exchange membrane by applying an electrical potential or voltage of the first polarity to the doping electrode in a state where the first ion exchange membrane is brought into contact a biological interface of the subject.

In this case, an increase in efficiency of administration of the active agent ion may be obtained because the transfer of a subject counter ion to the active agent solution reservoir can be blocked by the first ion exchange membrane.

In some embodiments, it may be preferable that: the electrode assembly further include a second ion exchange membrane of the second polarity placed on the front surface side of the doping layer; and the active agent solution reservoir be placed on the front surface side of the second ion exchange membrane.

An active agent may be administered to a subject in the same manner as that described above. In addition, changes to the active agent near the doping electrode during energization may be prevented or suppressed because the second ion exchange membrane can block the transfer of active agent ions to the side of the doping electrode.

In this case, the second ion exchange membrane and the doping layer are preferably joined integrally with each other. The integral joining can improve energization property between the doping layer and the second ion exchange membrane and simplify the assembly work of the electrode assembly. Therefore, automated production and mass production of the electrode assembly may be easily performed. Further, production cost may be reduced.

The second ion exchange membrane and the doping layer can be joined with each other by, for example, thermocompression bonding. Alternatively, the joining can be performed by forming the doping layer on the second ion exchange membrane by means of any of the various methods described above.

In some embodiments, the electrode assembly can further include: an electrolyte solution reservoir holding an electrolyte solution, the electrolyte solution reservoir being placed on the front surface side of the doping layer; and a first ion exchange membrane of the first polarity that is placed on the front surface side of the electrolyte solution reservoir and that is doped with active agent ions of the first polarity.

Such an electrode assembly can be used as an active electrode assembly in an iontophoresis device. Active agent ions with which the first ion exchange membrane is doped can be administered to a subject by applying an electrical potential or voltage of the first polarity to the doping electrode in a state where the first ion exchange membrane is brought into contact a biological interface of the subject.

Here, the electrolyte solution of the electrolyte solution reservoir serves to supply an ion of the first polarity for substituting the active agent ion in the first ion exchange membrane (hereinafter, the ion of the first polarity in the electrolyte solution is referred to as the "first electrolytic ion") and to supply an ion of the second polarity with which the doping layer is to be doped (hereinafter, the ion of the second polarity in the electrolyte solution is referred to as the "second electrolytic ion").

That is, the doping layer may capture the second electrolytic ion, thus doping the layer with the ion, where energization from the doping electrode to the electrolyte solution reservoir occurs. In addition, the active agent ion in the first ion exchange membrane is substituted by the first electrolytic ion from the electrolyte solution reservoir, so the active agent can be transferred to a subject.

The first ion exchange membrane can be doped with active agent ions by immersing the first ion exchange membrane in an active agent solution containing an appropriate concentration of active agent ion for a predetermined time period. The amount of the active agent ions with which the first ion exchange membrane is to be doped can be controlled by adjusting the concentration of the active agent ion, an immersion time, and the number of times of immersion in this case.

When the first electrolytic ion has a mobility larger than that of active agent ions, a higher priority may be placed on the transfer of the first electrolytic ion to a subject than that on the transfer of the active agent ion to the subject, so the efficiency of administration of an active agent may decrease. Use of a composition in which the first electrolytic ion has a mobility comparable to or smaller than that of the active agent ion may therefore be preferable for the electrolyte solution of the electrolyte solution reservoir. Alternatively, such reduction in efficiency of administration as described above can be prevented by using the active agent ion as the first electrolytic ion of the electrolyte solution reservoir.

The efficiency of administration of active agent ions may be increased because the first ion exchange membrane blocks the transfer of a subject counter ion to the electrolyte solution reservoir. Furthermore, the efficiency of administration of the active agent ion may be further increased because the active agent ion is held by the first ion exchange membrane as a member to be brought into direct contact a biological interface of a subject.

In addition, the stability of the active agent ion during storage may be improved, and the amount of a stabilizer, an antimicrobial agent, an antiseptic, or the like to be used can be reduced or the storage period of the device can be prolonged because the first ion exchange membrane holds the active agent ion by being doped with the ion (that is, the active agent ion binds to an ion exchange group in the ion exchange membrane). In addition, the stability of the administration of an active agent can be improved because the amount of the active agent ions with which the first ion exchange membrane is to be doped can be strictly adjusted. Furthermore, the production of the electrode assembly can be simplified because the first ion exchange membrane with which the active agent ion is doped is used instead of the active agent solution reservoir that must have been conventionally used in a wet state. Therefore, automated production and mass production of the electrode assembly may be easily performed. Further, production cost can be reduced.

In some embodiments, it may be preferable that: the electrode assembly further include a second ion exchange membrane of the second polarity placed on the front surface side of the electrolyte solution reservoir; and that the first ion exchange membrane be placed on the front surface side of the second ion exchange membrane.

An active agent may thus be administered to a subject in the same manner as that described above. In addition, changes to the active agent upon energization can be achieved because the second ion exchange membrane blocks the movement of active agent ions to the electrolyte solution reservoir.

It should be noted that the second ion exchange membrane should have a transport number less than one (for example, a transport number of 0.7 to 0.95) because the first electrolytic ion cannot transfer to the first ion exchange membrane in order to substitute the active agent ion when the transport number of the second ion exchange membrane is one. However, even the use of the second ion exchange membrane having a transport number from 0.7 to 0.95 can sufficiently prevent the transfer of the active agent ion to the electrolyte solution reservoir.

The term "transport number" as used herein is defined as a ratio of a charge amount conveyed by the passage of an active agent counter ion through the second ion exchange membrane to the total charge conveyed through the second ion exchange membrane when an electrical potential or voltage of the first polarity is applied to the side of an electrolyte solution held by the electrolyte solution reservoir in a state where the second ion exchange membrane is placed between the electrolyte solution and an active agent solution containing appropriate concentrations of active agent ion and active agent counter ion (for example, an active agent solution used for doping the first ion exchange membrane with the active agent ion).

In some embodiments, the electrolysis of water may occur at an interface between the first and second ion exchange membranes in some cases depending on energization conditions and the like. Therefore, a semi-permeable membrane capable of permitting the passage of at least the first electrolytic ion can be interposed between the first and second ion exchange membranes for preventing the electrolysis.

In some embodiments, the second ion exchange membrane may be replaced with a semi-permeable membrane. An effect similar to that described above can be achieved by using a semi-permeable membrane having a molecular weight cutoff property with which the passage of the first electrolytic ion is permitted while the passage of active agent ions is blocked.

The interface between the second ion exchange membrane and the first ion exchange membrane, each interface among the second ion exchange membrane, the semi-permeable membrane, and the first ion exchange membrane, and/or the interface between the semi-permeable membrane and the first ion exchange membrane can be joined integrally by means of, for example, thermocompression bonding. The integral joining can achieve an effect similar to that described above.

In some embodiments, it may be preferable that: the electrode assembly further include a second ion exchange membrane of the second polarity placed on the front surface side of the doping layer; and the electrolyte solution reservoir be placed on the front surface side of the second ion exchange membrane.

An active agent may thus be administered to a subject in the same manner as described above. In addition, changes to the active agent upon energization may be prevented because the second ion exchange membrane blocks the transfer of active agent ions to the doping electrode.

In some embodiments, the second ion exchange membrane can be replaced with a semi-permeable-membrane. An effect similar to that described above can be achieved by using, a semi-permeable membrane having a molecular weight cut-off property with which the passage of the first electrolytic ion can be permitted while the passage of active agent ions is blocked.

The interface between the doping electrode and the second ion exchange membrane or the interface between the doping electrode and the semi-permeable membrane can be joined integrally in the same manner as that described above. The integral joining can achieve an effect similar to that described above.

In some embodiments, it may be preferable that: the electrode assembly further include a first ion exchange membrane of the first polarity that is placed on the front surface side of the doping layer and that is doped with active agent ions of the first polarity; and the doping layer be doped with an ion of the first polarity.

Such an electrode assembly can be used as an active electrode assembly in an iontophoresis device. An electrical potential or voltage of the first polarity may be applied to the doping electrode in a state where the first ion exchange membrane is brought into contact a biological interface of a subject, whereby an ion of the first polarity in the doping layer transfers to the first ion exchange membrane, and active agent ions in the first ion exchange membrane substituted by the ion transfers into the subject.

In this case, energization from the doping electrode to the first ion exchange membrane is caused by the transfer of an ion of the first polarity in the doping layer to the first ion exchange membrane. Therefore, gas generation and undesirable ion generation may be suppressed.

Active agent ions may be administered to a subject from the ion exchange membrane of the first polarity doped with the active agent ion. Accordingly, effects similar to those described above, such as an increase in efficiency of administration of an active agent and an improvement of the stability of the active agent ion, may be achieved.

In addition, the doping layer may be doped with an ion of the first polarity for substituting active agent ions. Therefore, the electrolyte solution reservoir can be omitted, so the need for handling a wet member can be completely eliminated during production of the electrode assembly. Furthermore, the assembly of the electrode assembly requires only two members: the doping electrode and the first ion exchange membrane. Accordingly, the production of the electrode assembly is greatly simplified. In addition, the automated production and mass production of the electrode assembly can be extremely may be easily performed, and electrode assembly production costs may be significantly reduced.

The doping layer can be doped with an ion of the first polarity in the same manner as that described above, and the first ion exchange membrane can be doped with active agent ions in the same manner as that described above.

The ion of the first polarity with which the doping layer is to be doped may preferably be an ion having a mobility comparable to, or smaller than that of, the active agent ion, for reasons similar to those described above.

The interface between the doping electrode and the first ion exchange membrane may be joined integrally by means of, for example, thermocompression bonding. The integral joining can achieve an effect similar to that described above.

In some embodiments, it may be preferable that: the electrode assembly further include a second ion exchange membrane of the second polarity placed on the front surface side of the doping layer; and that the first ion exchange membrane be placed on the front surface side of the second ion exchange membrane.

An effect similar to that described above may thus be achieved. In addition, the active agent may be prevented from changing during energization because the second ion exchange membrane blocks the transfer of active agent ions to the doping layer.

It should be noted that the second ion exchange membrane should have a relatively low transport number (for example, a transport number of 0.7 to 0.95) in the same manner as described above owing to the same reason as that described above.

The second ion exchange membrane can be replaced with a semi-permeable membrane. An effect similar to that described above may be achieved by using a semi-permeable membrane having molecular weight cut-off property with which the passage of the first electrolytic ion can be permitted while the passage of active agent ions is blocked.

The interface between the doping electrode and the second ion exchange membrane or the semi-permeable membrane and/or the interface between the second ion exchange membrane or the semi-permeable membrane and the first ion exchange membrane can be joined integrally by means of, for example, thermocompression bonding. The integral joining may thus achieve an effect similar to that described above.

In some embodiments, the doping layer can be doped with active agent ions of the first polarity.

Such electrode assembly can be used as an active electrode assembly in an iontophoresis device. Active agent ions in the doping layer can be administered to a subject by applying an electrical potential or voltage of the first polarity to the doping electrode in a state where the doping layer is brought into contact with a biological interface of the subject without or with an intervening transport medium (e.g., gel, cream).

In this case, energization from the doping electrode to a biological interface of the subject is caused by the de-doping of the active agent ions with which the doping layer is doped to transfer to the subject. Therefore, the gas generation and undesirable ion generation may be suppressed.

An active electrode assembly can be made by using a single member (the doping electrode). Accordingly, production can be greatly simplified, and mass production can be easily achieved along with a reduction in production costs.

The doping layer doped with active agent ions of the first polarity functions as an ion exchange membrane of the first polarity. Therefore, the transfer of a subject counter ion to the doping layer upon administration of an active agent is blocked, so excellent performance can be obtained in terms of efficiency of administration of an active agent.

The doping layer can be doped with active agent ions through energization as a result of applying an electrical potential or voltage of the second polarity to the doping electrode in a state where the doping layer is immersed in an active agent solution containing an appropriate concentration of active agent ion.

In some embodiments, the electrode assembly may further include a first ion exchange membrane of the first polarity placed on the front surface side of the doping layer.

Such an electrode assembly can be used as an active electrode assembly in an iontophoresis device by doping the first ion exchange membrane, or the first ion exchange membrane and the doping layer, with active agent ions. The active agent ions with which the first ion exchange membrane or the first ion exchange membrane and the doping layer may be doped so that an agent can be administered to a subject by applying an electrical potential or voltage of the first polarity to the doping electrode in a state where the first ion exchange membrane is brought into contact with a biological interface of the subject without or with an intervening transfer medium.

The first ion exchange membrane can be doped with active agent ions through energization as a result of applying an electrical potential or voltage of the second polarity to the doping electrode in a state where the doping layer is immersed in an active agent solution containing an appropriate concentration of active agent ion.

Positive ions bound to an ion exchange group in the first ion exchange membrane and substituted by the active agent ion from the active agent solution can transfer to the doping layer, thus doping the layer with the ion. Alternatively, the doping layer may be doped with the active agent ion of the active agent solution as well depending on conditions for performing the doping.

Energization from the doping electrode to the first ion exchange membrane upon administration of an active agent is caused by the transfer of the positive ion or active agent ion with which the doping layer is doped as described above to the first ion exchange membrane. Therefore, gas generation and undesirable ion generation may be prevented. The active agent ions with which the first ion exchange membrane is doped is substituted by an ion transferring from the doping layer, to thereby transfer to a subject.

The efficiency of administration of an active agent can thus be increased because the first ion exchange membrane blocks the transfer of a subject counter ion to the doping layer.

Furthermore, no structure is used where the doping layer is brought into direct contact a biological interface of a subject. Therefore, an active agent can be safely administered even when a doping layer which is not brought into contact a biological interface of a subject.

The electrode assembly may comprise only two members: the doping electrode and the first ion exchange membrane. In addition, there is no need to handle wet members during production of an active electrode assembly. Therefore, the production of the electrode assembly is greatly simplified. As a result, the automated production and mass production of the electrode assembly can be easily performed. Further, production costs for the electrode assembly can be significantly reduced.

The doping of the first ion exchange membrane with the active agent ion may be performed at any point in time from the initial production step through to immediately before the device is used (the administration of an active agent to a subject).

The interface between the doping electrode and the first ion exchange membrane can be joined integrally by means of, for example, thermocompression bonding. The integral joining can thus achieve effects similar to those described above.

In yet even another aspect, the present disclosure is directed to an iontophoresis device comprising: an active electrode assembly holding active agent ions of a first polarity; and a counter electrode assembly as a counter electrode of the active electrode assembly. The counter electrode assembly comprises an electrode in which a doping layer made of a substance effecting an electrochemical reaction owing to the doping or de-doping of an ion is formed.

In such an iontophoresis device, an electrical potential or of the second polarity is applied to the doping electrode of the counter electrode assembly upon administration of an active agent, but the generation of gases such as hydrogen, oxygen, or chlorine may be prevented, the generation of undesirable ions such as hydrogen or hydroxide ions may be prevented, and the generation of hypochlorous acid at the counter electrode assembly may be prevented.

That is, when the doping layer is not doped with ions of the second polarity, energization in the counter electrode assembly is caused by the transfer of ions of the first polarity on a biological interface of a subject or in the subject to the doping layer such that the layer is doped with the ion. When the doping layer is doped with ions of the second polarity, the energization is caused by the de-doping of the second polarity ions from the doping layer to transfer to the subject, in addition to doping the doping layer with the ion of the first polarity.

The active electrode assembly in some embodiments may hold active agent ions at an active agent solution reservoir holding an active agent solution as previously described. Alternatively, the active electrode assembly may hold the active agent ion doped into the first ion exchange membrane or the doping layer also as previously described. In addition, the active electrode assembly may not require a doping electrode.

In some embodiments, the counter electrode assembly may preferably further comprise a third ion exchange membrane of the first polarity placed on the front surface side of the doping layer.

In such an electrode assembly, energization is performed in a state where the third ion exchange membrane is brought into contact a biological interface of a subject. Therefore, an iontophoresis device capable of administering active agent ions without bringing the doping layer into direct contact a biological interface is realized.

It should be noted that energization in the counter electrode assembly is mainly caused by the transfer of an ion of the first polarity on a biological interface of a subject or in the subject to the doping layer such that the layer is doped with the ion.

It may be preferable that the counter electrode assembly further include a third ion exchange membrane of the second polarity that is placed on the front surface side of the doping layer, and that the doping layer be doped with an ion of the second polarity.

Such electrode assembly realizes an iontophoresis device capable of administering active agent ions without bringing the doping layer into direct contact a biological interface.

It should be noted that energization in the counter electrode assembly is mainly caused by the de-doping of an ion of the second polarity from the doping layer to transfer to the side of a subject.

The interface between the doping electrode and the third ion exchange membrane can be joined integrally by means of, for example, thermocompression bonding. The integral joining can achieve an effect similar to that described above.

In some embodiments, the counter electrode assembly can further include a second electrolyte solution reservoir that holds an electrolyte solution, the second electrolyte solution reservoir being placed on the front surface side of the doping layer. In this case, energization is caused, for example, by the transfer of the first electrolytic ions in the second electrolyte solution reservoir to the doping layer such that the layer is doped with the ions, and the transfer of the second electrolytic ions to a subject.

It may be preferable that the doping electrode of any one of the previously described embodiments further include a conductive base material; and the doping layer be stacked on the conductive base material.

As described above, the conductivity of the doping layer may be improved by doping the layer with electron acceptor or electron donor ions. Alternatively, an iontophoresis device capable of administering an active agent with improved efficiency may be made by placing the doping layer on the conductive base material to reduce the surface resistance of the doping electrode in such a manner that energization can be performed from the doping layer at a uniform current density.

The doping layer can be formed on the conductive base material by using, for example, a method comprising: applying to the conductive base material a powder-like conductive polymer blended with an appropriate polymer binder or a solution of a conductive polymer in an appropriate polar organic solvent; and subjecting the resultant to curing, solvent removal, or the like. Alternatively, another method that may be used comprises: immersing the conductive base material in a solution of a monomer for producing a conductive polymer; and performing electrolytic polymerization.

In some embodiments, the conductive base material is preferably a conductive sheet made of a carbon fiber or carbon fiber paper.

The doping electrode can thus be formed without using a metallic member. As a result, metal ions, which may elute from a metallic member and which may be harmful, can be prevented from transferring to a subject to do harm to the subject. In addition, energization can occur from the doping electrode at a uniform current density because the carbon fiber or carbon fiber paper is a material having a low surface resistance. An iontophoresis device including an electrode assembly having enough flexibility to follow the irregularities of a biological interface of a subject or the movement of the subject can be provided because the carbon fiber or carbon fiber paper is a material having high flexibility.

In this case, an electrode described in JP 2004-317317 A or JP 2005-222892 A by the applicant, both incorporated herein by reference in their entirety, may be used.

That is, some embodiments, the electrode can further include a terminal member with carbon mixed in a polymer matrix, the terminal member being attached to the conductive sheet. Alternatively, the electrode can further include an extension portion that is formed integrally with the conductive sheet and that is made of a carbon fiber or carbon fiber paper.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

Figure 1:
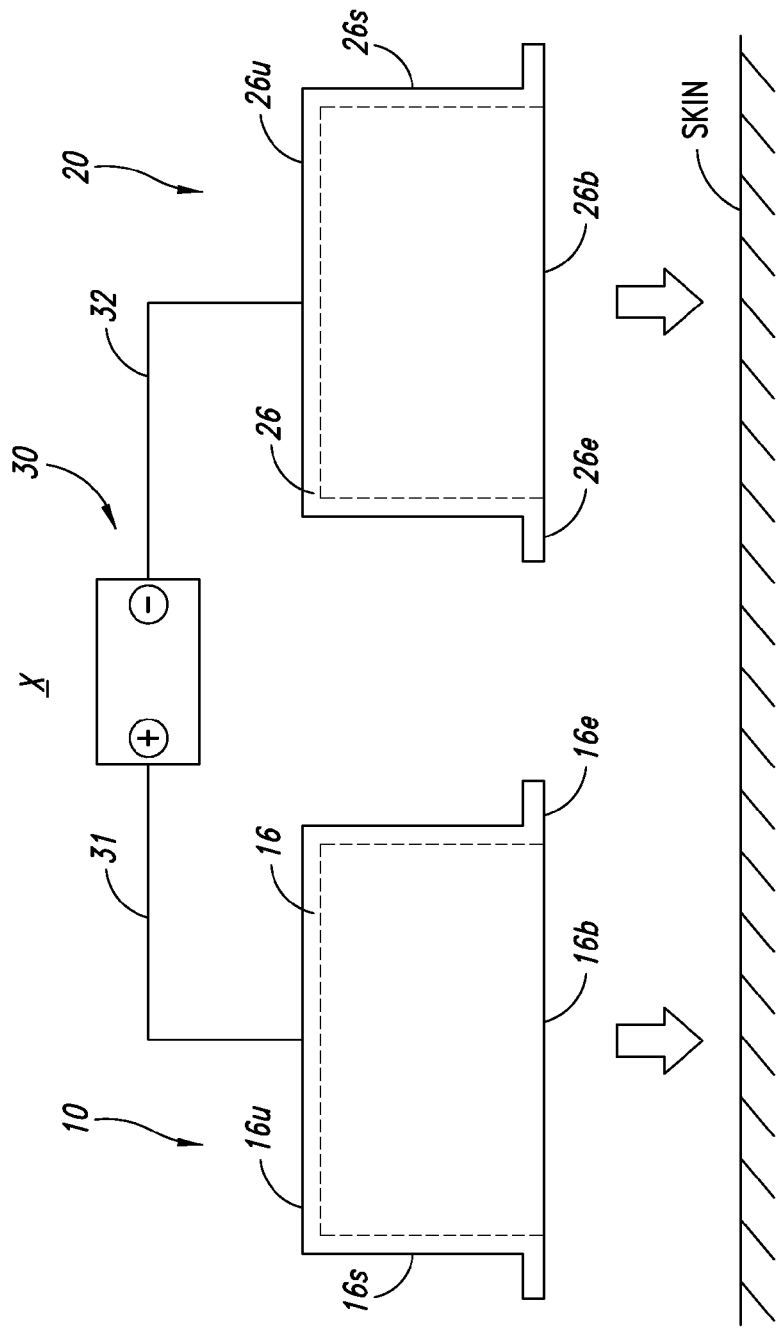
FIG. 1 is an explanatory view showing the schematic constitution of an iontophoresis device according to an embodiment of the present invention.
Figure 2A:
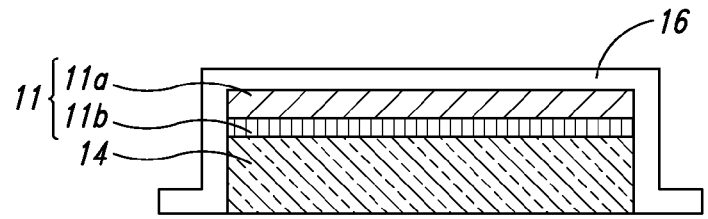
FIGS. 2A to 2D are explanatory sectional views each showing the constitution of an active electrode assembly of an iontophoresis device according to an embodiment of the present invention.
Figure 2B:
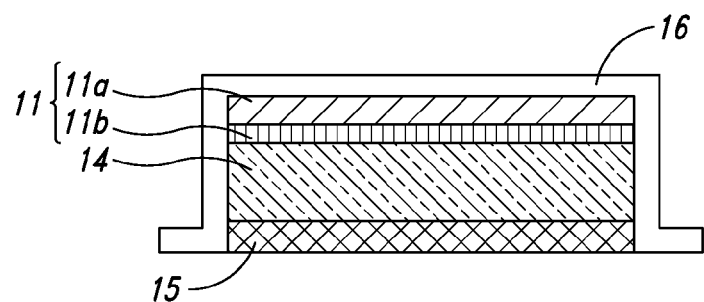
Figure 2C:
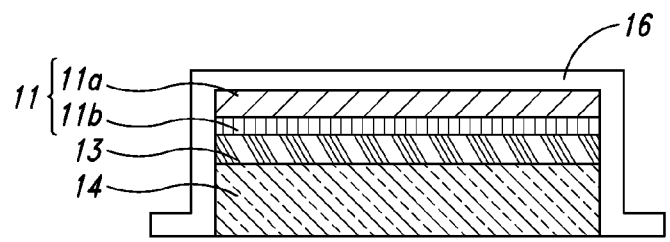
Figure 2D:
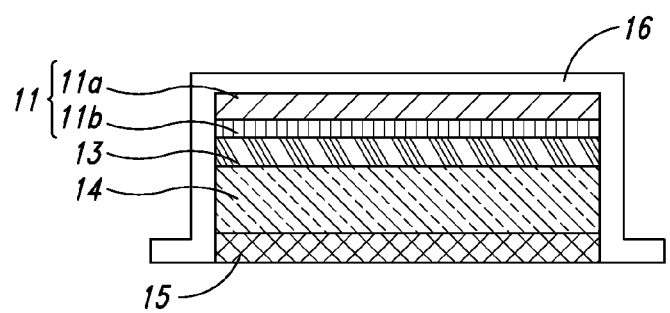

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with iontophoresis devices, controllers, voltage or current sources and/or membranes have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to." Reference throughout this specification to "one embodiment," or "an embodiment," or "another embodiment" means that a particular referent feature, structure, or characteristic described in connection with the embodiment is included in at least one embodiment. Thus, the appearances of the phrases "in one embodiment," or "in an embodiment," or "another embodiment" in various places throughout this specification are not necessarily all referring to the same embodiment. Further more, the particular features, structures, or characteristics may be combined in any suitable manner in one or more embodiments.

It should be noted that, as used in this specification and the appended claims, the singular forms "a," "an," and "the" include plural referents unless the content clearly dictates otherwise. Thus, for example, reference to a system for evaluating an iontophoretic active agent delivery including "a controller" comprises a single controller, or two or more controllers. It should also be noted that the term "or" is generally employed in its sense including "and/or" unless the content clearly dictates otherwise.

As used herein the term "membrane" means a boundary, a layer, barrier, or material, which may, or may not be permeable. The term "membrane" may further refer to an interface.

Unless specified otherwise, membranes may take the form a solid, liquid, or gel, and may or may not have a distinct lattice, non cross-linked structure, or cross-linked structure.

As used herein the term "ion selective membrane" means a membrane that is substantially selective to ions, passing certain ions while blocking passage of other ions. An ion selective membrane for example, may take the form of a charge selective membrane, or may take the form of a semi-permeable membrane.

As used herein the term "charge selective membrane" means a membrane that substantially passes and/or substantially blocks ions based primarily on the polarity or charge carried by the ion. Charge selective membranes are typically referred to as ion exchange membranes, and these terms are used interchangeably herein and in the claims. Charge selective or ion exchange membranes may take the form of a cation exchange membrane, an anion exchange membrane, and/or a bipolar membrane. A cation exchange membrane substantially permits the passage of cations and substantially blocks anions. Examples of commercially available cation exchange membranes include those available under the designators NEOSEPTA, CM-1, CM-2, CMX, CMS, and CMB from Tokuyama Co., Ltd. Conversely, an anion exchange membrane substantially permits the passage of anions and substantially blocks cations. Examples of commercially available anion exchange membranes include those available under the designators NEOSEPTA, AM-1, AM-3, AMX, AHA, ACH and ACS also from Tokuyama Co., Ltd.

Examples of cation exchange groups that may be introduced into the cation exchange membrane include sulfonic groups, carboxylic groups, and phosphoric groups. The transport number of an ion exchange membrane can be controlled depending on the kind of a cation exchange group to be introduced. For example, the use of a sulfonic group as a strong acidic group provides a cation exchange membrane having a high transport number.

Examples of anion exchange groups that may be introduced into the anion exchange membrane include primary amino groups, secondary amino groups, tertiary amino groups, quaternary ammonium groups, pyridyl groups, imidazole groups, quaternary pyridinium groups, and quaternary imidazolium groups. The transport number of an ion exchange membrane can be controlled depending on the kind of an anion exchange group to be introduced. For example, the use of a quaternary ammonium group or a quaternary pyridinium group as a strong basic group provides an anion exchange membrane having a high transport number.

Known examples of a treatment for introducing a cation exchange group include various approaches such as sulfonation, chlorosulfonation, phosphonation, and hydrolysis. Known examples of a treatment for introducing an anion exchange group include various approaches such as amination and alkylation. The transport number of an ion exchange membrane can be adjusted by adjusting conditions under which a treatment for introducing an ion exchange group is performed.

In addition, the transport number of an ion exchange membrane can be adjusted depending on, for example, the amount of an ion exchange resin in the ion exchange membrane and the pore size of the membrane. For example, in the case of an ion exchange membrane of a type in which a porous film is filled with an ion exchange resin, an ion exchange membrane obtained by filling a porous film with an ion exchange resin at a filling ratio of preferably 5 to 95 mass %, more preferably 10 to 90 mass %, or particularly preferably 20 to 60 mass % can be used, the porous film having formed thereon a large number of small pores having a mean pore size of preferably 0.005 to 5.0 µm, more preferably 0.01 to 2.0 µm, or most preferably 0.02 to 0.2 µm (a mean flow pore size measured in conformance with the bubble point method (JIS K3832-1990)) at a porosity of preferably 20 to 95%, more preferably 30 to 90%, or most preferably 30 to 60% and having a thickness of preferably 5 to 140 µm, more preferably 10 to 120 µm, or most preferably 15 to 55 µm. The transport number of the ion exchange membrane can be adjusted depending also on the mean pore size of the small pores and the porosity of the porous film, and the filling ratio of the ion exchange resin.

As used herein, the term "semi-permeable membrane" means a membrane that is substantially selective based on a size or molecular weight of the ion. Thus, a semi-permeable membrane substantially passes ions of a first molecular weight or size, while substantially blocking passage of ions of a second molecular weight or size, greater than the first molecular weight or size. In some embodiments, a semi-permeable membrane may permit the passage of some molecules a first rate, and some other molecules a second rate different than the first. In yet further embodiments, the "semi-permeable membrane" may take the form of a selectively permeable membrane allowing only certain selective molecules to pass through it.

As used herein, the term "porous membrane" means a membrane that is not substantially selective with respect to ions at issue. For example, a porous membrane is one that is not substantially selective based on polarity, and not substantially selective based on the molecular weight or size of a subject element or compound.

As used herein and in the claims, the term "gel matrix" means a type of reservoir, which takes the form of a three dimensional network, a colloidal suspension of a liquid in a solid, a semi-solid, a cross-linked gel, a non cross-linked gel, a jelly-like state, and the like. In some embodiments, the gel matrix may result from a three dimensional network of entangled macromolecules (e.g., cylindrical micelles). In some embodiment a gel matrix may include hydrogels, organogels, and the like. Hydrogels refer to three-dimensional network of, for example, cross-linked hydrophilic polymers in the form of a gel and substantially comprising water. Hydrogels may have a net positive or negative charge, or may be neutral.

A used herein, the term "reservoir" means any form of mechanism to retain an element, compound, pharmaceutical composition, active agent, and the like, in a liquid state, solid state, gaseous state, mixed state and/or transitional state. For example, unless specified otherwise, a reservoir may include one or more cavities formed by a structure, and may include one or more ion exchange membranes, semi-permeable membranes, porous membranes and/or gels if such are capable of at least temporarily retaining an element or compound. Typically, a reservoir serves to retain a biologically active agent prior to the discharge of such agent by electromotive force and/or current into the biological interface. A reservoir may also retain an electrolyte solution.

A used herein, the term "active agent" refers to a compound, molecule, or treatment that elicits a biological response from any host, animal, vertebrate, or invertebrate, including for example fish, mammals, amphibians, reptiles, birds, and humans. Examples of active agents include therapeutic agents, pharmaceutical agents, pharmaceuticals (e.g., an active agent, a therapeutic compound, pharmaceutical salts, and the like) non-pharmaceuticals (e.g., cosmetic substance, and the like), a vaccine, an immunological agent, a local or general anesthetic or painkiller, an antigen or a protein or peptide such as insulin, a chemotherapy agent, an anti-tumor agent. In some embodiments, the term "active agent" further refers to the active agent, as well as its pharmacologically active salts, pharmaceutically acceptable salts, prodrugs, metabolites, analogs, and the like. In some further embodiment, the active agent comprises at least one ionic, cationic, ionizable and/or neutral therapeutic drug and/or pharmaceutical acceptable salts thereof. In yet other embodiments, the active agent may include one or more "cationic active agents" that are positively charged, and/or are capable of forming positive charges in aqueous media. For example, many biologically active agents have functional groups that are readily convertible to a positive ion or can dissociate into a positively charged ion and a counter ion in an aqueous medium. While other active agents may be polarized or polarizable, that is exhibiting a polarity at one portion relative to another portion. For instance, an active agent having an amino group can typically take the form an ammonium salt in solid state and dissociates into a free ammonium ion ($NH_4+$) in an aqueous medium of appropriate pH. The term "active agent" may also refer to neutral agents, molecules, or compounds capable of being delivered via electro-osmotic flow. The neutral agents are typically carried by the flow of, for example, a solvent during electrophoresis. Selection of the suitable active agents is therefore within the knowledge of one skilled in the art.

Non-limiting examples of such active agents include lidocaine, articaine, and others of the -caine class; morphine, hydromorphone, fentanyl, oxycodone, hydrocodone, buprenorphine, methadone, and similar opiod agonists; sumatriptan succinate, zolmitriptan, naratriptan HCl, rizatriptan benzoate, almotriptan malate, frovatriptan succinate and other 5-hydroxytryptamine 1 receptor subtype agonists; resiquimod, imiquidmod, and similar TLR 7 and 8 agonists and antagonists; domperidone, granisetron hydrochloride, ondansetron and such anti-emetic drugs; zolpidem tartrate and similar sleep inducing agents; L-dopa and other anti-Parkinson's medications; aripiprazole, olanzapine, quetiapine, risperidone, clozapine and ziprasidone as well as other neuroleptica; diabetes drugs such as exenatide; as well as peptides and proteins for treatment of obesity and other maladies.

As used herein and in the claims, the term "subject" generally refers to any host, animal, vertebrate, or invertebrate, and includes fish, mammals, amphibians, reptiles, birds, and particularly humans.

The headings provided herein are for convenience only and do not interpret the scope or meaning of the embodiments.

Hereinafter, embodiments will be described with reference to the drawings.

FIG. 1 is an explanatory view showing the schematic constitution of an iontophoresis device X according to one illustrated embodiment.

An iontophoresis device for administering an active agent whose active agent component dissociates into positive active agent ions (for example, lidocaine hydrochloride or morphine hydrochloride) is taken as an example. An iontophoresis device for administering an active agent whose active agent component dissociates into negative ions (for example, ascorbic acid), the device being capable of achieving substantially an effect similar to that of the following embodiment, can be achieved by reversing the polarity of an electric power source, the polarity of each ion exchange membrane, and the polarity of an ion with which a doping layer or a cation exchange membrane is doped in the following description.

Referring to FIG. 1, the iontophoresis device X comprises: an electric power source 30; an active electrode assembly 10 connected to the positive pole of the electric power source 30 via an electric supply line 31; and a counter electrode assembly 20 connected to the negative pole of the electric power source 30 via an electric supply line 32.

The active electrode assembly 10/the counter electrode assembly 20 is a container 16/26 comprising an upper wall 16u/26u and an outer peripheral wall 16s/26s. A space capable of housing various structures to be described later is formed in the container 16/26, and a lower surface 16b/26b of the container 16/26 is opened.

The container 16 or 26 can be formed of a variety of materials such as a plastic, but is preferably formed of a flexible material capable of: preventing the evaporation of water from the inside of the container and the penetration of foreign matter from the outside; and following the irregularities of a biological interface of a subject or the movement of the subject. In addition, a removable liner comprising an appropriate material for preventing the evaporation of water and the mixing of foreign matter during storage of the iontophoresis device X can be stuck to the lower surface 16b/26b of the container 16/26. An adhesive layer for improving adhesion to a biological interface upon administration of an active agent can be arranged on a lower end portion 16e/26e of the outer peripheral wall 16s/26s.

The container 16 or 26 is not necessarily arranged in the absence of a wet member such as an active agent solution reservoir or an electrolyte solution reservoir (a member with a high water content) like active electrode assemblies 10H to 10K and counter electrode assemblies 20A to 20C to be described later.

A battery, a constant voltage device, a constant current device, a constant voltage/current device, or the like can be used as the electric power source 30. It is preferable to use a constant current device whose current can be adjusted in the range of 0.01 to 1.0 $mA/cm^2$, or preferably 0.01 to 0.5 $mA/cm^2$, and which operates under safe voltage conditions, specifically at 50 V or less, or preferably 30 V or less.

FIGS. 2A to 2D are explanatory sectional views showing the constitutions of active electrode assemblies 10A to 10D each of which can be used as the active electrode assembly 10 of the iontophoresis device X.

The active electrode assembly 10A comprises: an electrode 11 having a conductive base material 11a connected to the electric supply line 31 and a doping layer 11b formed on one surface of the base material 11a and comprising polyaniline; and an active agent solution reservoir 14 holding an active agent solution in contact with the doping layer 11b.

The active agent solution is a solution of an active agent whose active agent component dissociates into positive active agent ions. The active agent solution reservoir 14 can hold the active agent solution in a liquid state, or can hold the active agent solution by impregnating an absorbing carrier such as a gauze, filter paper, or a gel with the active agent solution.

In the active electrode assembly 10A, a positive voltage is applied to the electrode 11 in a state where the active agent solution reservoir 14 is brought into contact a biological interface of a subject (without or with an intervening transport material), whereby active agent ions in the active agent solution reservoir 14 is administered to the subject. In this case, energization from the electrode 11 to the active agent solution reservoir 14 is entirely or partially caused by the transfer of negative ions in the active agent solution to the doping layer 11b such that the layer is doped with the ion. Therefore, the generation of oxygen gas or chlorine gas, and the production of hydrogen ions or hypochlorous acid due to energization can be prevented or at least reduced.

The doping layer 11b has a thickness of typically 10 nm to 100 µm, or preferably 1 to 10 µm.

The active electrode assembly 10B comprises: the electrode 11 and the active agent solution reservoir 14, which are identical to those of the active electrode assembly 10A; and a cation exchange membrane 15 placed on the front surface side of the active agent solution reservoir 14.

The active electrode assembly 10B achieves an effect similar to that of the active electrode assembly 10A concerning the prevention of: the generation of a gas; or the production of undesirable ions upon energization. The active electrode assembly 10B achieves an additional effect, that is, an increase in efficiency of administration of active agent ions because the transfer of a subject 20 counter ion to the active agent solution reservoir 14 is blocked by the cation exchange membrane 15.

The active electrode assembly 10C comprises: the electrode 11 and the active agent solution reservoir 14 identical to those of the active electrode assembly 10A; and an anion exchange membrane 13 placed between the electrode 11 and the active agent solution reservoir 14.

In the active electrode assembly 10C, energization from the electrode 11 to the active agent solution reservoir 14 is caused by the transfer of negative ions in the active agent solution reservoir 14 to the doping layer 11b via the anion exchange membrane 13 such that the layer is doped with the ion. Therefore, the active electrode assembly 10C may achieve an effect similar to that of the active electrode assembly 10A concerning the prevention of: gas generation, and the production of undesirable ions upon energization.

Furthermore, the active electrode assembly 10C may achieve an additional effect, that is, the prevention of the decomposition and alteration of an active agent upon energization because the transfer of active agent ions in the active agent solution reservoir 14 to the doping layer 11b is blocked by the anion exchange membrane 13.

The active electrode assembly 10D comprises: the electrode 11 and the active agent solution reservoir 14 identical to those of the active electrode assembly 10A; the anion exchange membrane 13 placed between the electrode 11 and the active agent solution reservoir 14; and the cation exchange membrane 15 placed on the front surface side of the active agent solution reservoir 14.

Therefore, the active electrode assembly 10D may achieve an effect similar to that of the active electrode assembly 10A concerning the prevention of: gas generation and the production of undesirable ions upon energization. The active electrode assembly 10D may achieve additional effects, that is, the prevention of the decomposition and alteration of an active agent upon energization and an increase in efficiency of administration of the active agent as in the case of the active electrode assemblies 10B and 10C.

In each of the active electrode assemblies 10C and 10D, the electrode 11 and the anion exchange membrane 13 can be joined and integrated with each other by means of an approach such as thermocompression bonding. This action can improve a state of energization from the electrode 11 to the anion exchange membrane 13 or simplify the assembly work of each of the active electrode assemblies 10C and 10D.

Figure 3A:
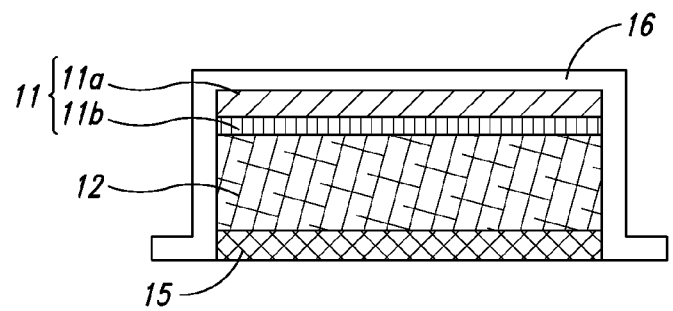
FIGS. 3A to 3C are explanatory sectional views each showing the constitution of an active electrode assembly of an iontophoresis device according to an embodiment of the present invention.
Figure 3B:
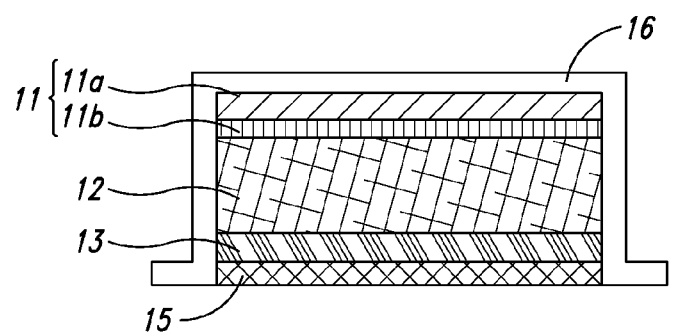
Figure 3C:
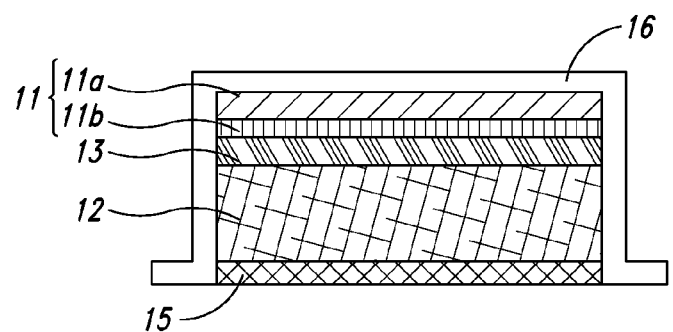

FIGS. 3A to 3C are explanatory sectional views showing the constitutions of active electrode assemblies 10E to 10G according to still another aspect each of which can be used as the active electrode assembly 10 of the iontophoresis device X.

The active electrode assembly 10E comprises: the electrode 11 identical to that of the active electrode assembly 10A; an electrolyte solution reservoir 12 holding an electrolyte solution in contact with the doping layer 11b; and the cation exchange membrane 15 placed on the front surface side of the electrolyte solution reservoir 12 and doped with a positive active agent ion.

In the active electrode assembly 10E, a positive electrical potential or voltage is applied to the electrode 11 in a state where the cation exchange membrane 15 is brought into contact a biological interface of a subject, whereby the active agent ions with which the cation exchange membrane 15 is doped is administered to the subject.

An active agent can thus be administered with high efficiency because the cation exchange membrane 15 at least partially blocks the transfer of a subject counter ion to the electrolyte solution reservoir 12.

In addition, energization from the electrode 11 to the electrolyte solution reservoir 12 is entirely or partially caused by the transfer of negative ions in the electrolyte solution to the doping layer 11b such that the layer is doped with the ion. Therefore, the generation of oxygen gas or chlorine gas, and the production of hydrogen ions or hypochlorous acid due to energization can be prevented or at least reduced.

Energization from the electrolyte solution reservoir 12 to the cation exchange membrane 15 is caused by the transfer of positive ions in the electrolyte solution reservoir 12 to the cation exchange membrane 15. The positive ion is substituted by active agent ions that have transferred to a subject, to thereby bind to an ion exchange group in the cation exchange membrane 15.

The electrolyte solution reservoir 12 of the active electrode assembly 10E may hold the electrolyte solution in a liquid state, or may hold the electrolyte solution by impregnating an absorbing carrier such as a gauze, filter paper, or a gel with the electrolyte solution.

When a positive ion in the electrolyte solution reservoir 12 has a mobility larger than that of active agent ions, the transfer of the positive ion to a subject preferentially may occur, so the efficiency of administration of an active agent may reduce. Therefore, the electrolyte solution of the electrolyte solution reservoir 12 preferably has a constitution free of positive ions having a mobility comparable to or larger than that of active agent ions.

The cation exchange membrane 15 can be doped with active agent ions by immersing the cation exchange membrane 15 in an active agent solution containing an appropriate concentration of the active agent ion.

The active electrode assembly 10F comprises: the electrode 11, the electrolyte solution reservoir 12, and the cation exchange membrane 15 identical to those of the active electrode assembly 10E; and further the anion exchange membrane 13 placed between the electrolyte solution reservoir 12 and the cation exchange membrane 15.

The active electrode assembly 10F may achieve an effect similar to that of the active electrode assembly 10E concerning the prevention of: the generation of a gas; or the production of undesirable ions upon energization. The active electrode assembly 10F may achieve an additional effect, that is, the prevention of the alteration of an active agent near the electrode 11 upon energization because the transfer of the active agent ions with which the cation exchange membrane 15 is doped to the electrolyte solution reservoir 12 is blocked by the anion exchange membrane 13.

Causing energization from the electrolyte solution reservoir 12 to the cation exchange membrane 15 in the active electrode assembly 10F requires that a positive ion in the electrolyte solution reservoir 12 should pass through the anion exchange membrane 13 to transfer to the cation exchange membrane 15. Therefore, an anion exchange membrane having a relatively low transport number is used for the anion exchange membrane 13.

In the active electrode assembly 10F, the electrolysis of water occurs at an interface between the anion exchange membrane 13 and the cation exchange membrane 15 in some cases depending on energization conditions and the like. Therefore, a semi-permeable membrane capable of permitting the passage of at least a positive ion in the electrolyte solution reservoir 12 can be further placed between the anion exchange membrane 13 and the cation exchange membrane 15 for preventing the electrolysis. The interface between the anion exchange membrane 13 and the cation exchange membrane 15 or each interface among the anion exchange membrane 13, the semi-permeable membrane, and the cation exchange membrane 15 can be joined by means of an approach such as thermocompression bonding. This action can improve energization property between them and handleability thereof.

The anion exchange membrane 13 in the active electrode assembly 10F permits the passage of a positive ion in the electrolyte solution reservoir 12. An effect similar to that described above can be obtained even when the membrane is replaced with a semi-permeable membrane capable of blocking the passage of active agent ions.

The active electrode assembly 10G comprises: the electrode 11, the electrolyte solution reservoir 12, and the cation exchange membrane 15 identical to those of the active electrode assembly 10E; and the anion exchange membrane 13 placed between the electrode 11 and the electrolyte solution reservoir 12.

In the active electrode assembly 10G, energization from the electrode 11 to the electrolyte solution reservoir 12 is caused by the transfer of negative ions in the electrolyte solution reservoir 12 to the doping layer via the anion exchange membrane such that the layer is doped with the ion. Therefore, the active electrode assembly 10G may achieve an effect similar to that of the active electrode assembly 10E concerning the prevention of: the generation of a gas; or the production of undesirable ions upon energization.

Energization from the electrolyte solution reservoir 12 to the cation exchange membrane 15 occurs in the same manner as in the case of the active electrode assembly 10E. Furthermore, an additional effect, that is, the prevention of the decomposition and alteration of an active agent upon energization may be achieved because the transfer of the active agent ions with which the cation exchange membrane 15 is doped to the doping layer 11b is blocked by the anion exchange membrane 13.

The electrode 11 and the anion exchange membrane 13 may be joined and integrated with each other by means of an approach such as thermocompression bonding, whereby energization property between them and the handleability of them can be improved.

Figure 4A:
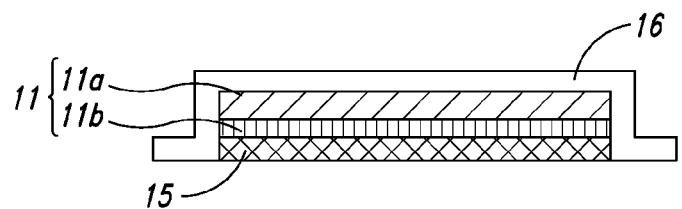
FIGS. 4A and 4B are explanatory sectional views each showing the constitution of an active electrode assembly of an iontophoresis device according to an embodiment of the present invention.
Figure 4B:
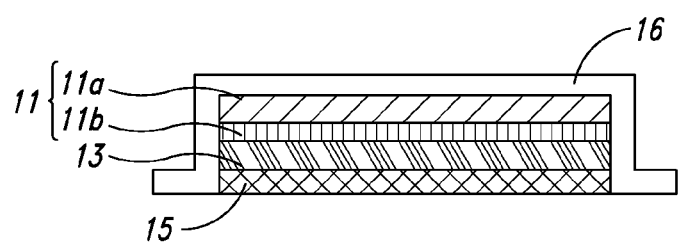

FIGS. 4A and 4B are explanatory sectional views showing the constitutions of active electrode assemblies 10H and 101 according to still another aspect each of which can be used as the active electrode assembly 10 of the iontophoresis device X.

The active electrode assembly 10H comprises: the electrode 11 having the conductive base material 11a connected to the electric supply line 31 and the doping layer 11b formed on one surface of the base material 11a and doped with a positive ion; and the cation exchange membrane 15 placed on the front surface side of the doping layer 11b and doped with active agent ions.

In the active electrode assembly 10H, a positive electrical potential or voltage is applied to the electrode 11 in a state where the cation exchange membrane 15 is brought into contact a biological interface of a subject (without or with an intervening transfer medium), whereby the active agent ions with which the cation exchange membrane 15 is doped is administered to the subject. As a result, an active agent may be administered with high efficiency in the same manner as in the case of the active electrode assembly 10E.

In the active electrode assembly 10H, energization from the electrode 11 to the cation exchange membrane 15 is caused by the transfer of the positive ion with which the doping layer 11b is doped to the cation exchange membrane 15. Therefore, the generation of oxygen gas or chlorine gas, or the production of hydrogen ions or hypochlorous acid due to energization, may be prevented or reduced. The positive ion that has transferred from the doping layer 11b to the cation exchange membrane 15 is substituted by active agent ions that have transferred to a subject, to thereby bind to an ion exchange group in the cation exchange membrane 15.

Referring to FIGS. 4A and 4B, the active electrode assembly 10H has a simple structure comprising only the electrode 11 and the cation exchange membrane 15, and there is no need to handle a wet member upon assembly of the active electrode assembly 10H. Therefore, the automation of the production of the active electrode assembly 10H and the mass production of the active electrode assembly 10H can be extremely easily performed, and the production cost of the active electrode assembly 10 can be significantly reduced.

The electrode 11 and the cation exchange membrane 15 may be joined and integrated with each other by means of an approach such as thermocompression bonding, whereby energization property between them and the handleability of them can be improved.

The doping layer 11b of the active electrode assembly 10H can be doped with a positive ion through energization with the electrode 11 as a negative pole in a state where the doping layer 11b is immersed in an appropriate electrolyte solution. In addition, the cation exchange membrane 15 can be doped with active agent ions in the same manner as that described above with respect to the active electrode assembly 10E.

The doping layer 11b is preferably doped with a positive ion having a mobility smaller than that of active agent ions owing to the same reason as that described above with respect to the active electrode assembly 10E. The positive ion can be active agent ions identical to or different from the active agent ions with which the cation exchange membrane 15 is doped.

The active electrode assembly 101 comprises: the electrode 11 and the cation exchange membrane identical to those of the active electrode assembly 10H; and the anion exchange membrane 13 placed between the electrode 11 and the cation exchange membrane 15.

In the active electrode assembly 101, as in the case of the active electrode assembly 10H, the generation of oxygen gas or chlorine gas, and the production of hydrogen ions or hypochlorous acid upon administration of an active agent may be prevented, and there is no need to handle a wet member upon assembly. In addition, an additional effect, that is, the prevention of the decomposition and alteration of an active agent upon energization may be achieved because the transfer of the active agent ions with which the cation exchange membrane 15 is doped to the electrolyte solution reservoir 12 is blocked by the anion exchange membrane 13.

Causing energization from the electrode 11 to the cation exchange membrane 15 in the active electrode assembly 101 requires that the positive ion with which the doping layer 11b is doped should pass through the anion exchange membrane 13 to transfer to the cation exchange membrane 15. Therefore, an anion exchange membrane having a relatively low transport number may be used for the anion exchange membrane 13.

The electrode 11, the anion exchange membrane 13, and the cation exchange membrane may be joined and integrated with one another by means of an approach such as thermocompression bonding, whereby energization property among them and the handleability of them may be improved.

An effect similar to that described above may be achieved even when the anion exchange membrane 13 in the active electrode assembly 10I is replaced with a semi-permeable membrane that blocks the passage of active agent ions while permitting the passage of a positive ion in the electrolyte solution reservoir 12.

Figure 5A:
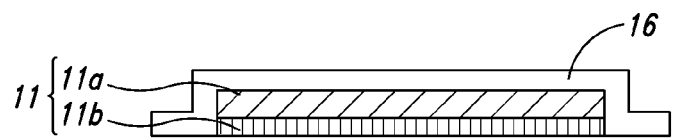
FIGS. 5A and 5B are explanatory sectional views each showing the constitution of an active electrode assembly of an iontophoresis device according to an embodiment of the present invention.
Figure 5B:
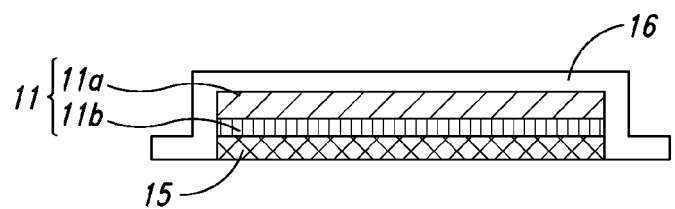
Figure 6A:
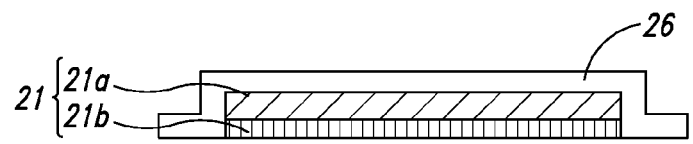
FIGS. 6A to 6D are explanatory sectional views each showing the constitution of a counter electrode assembly of an iontophoresis device according to an embodiment of the present invention.
Figure 6B:
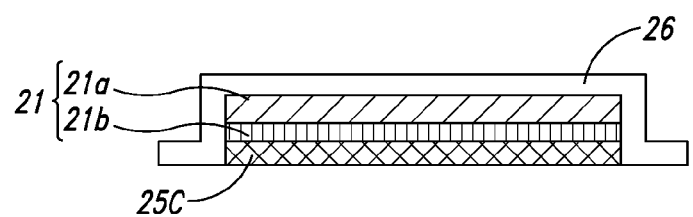
Figure 6C:
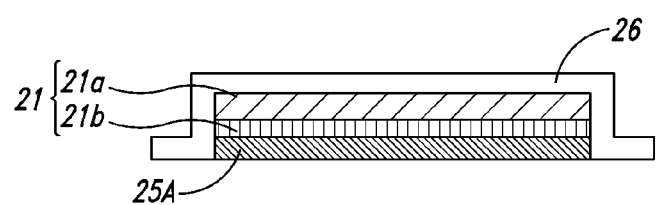
Figure 6D:
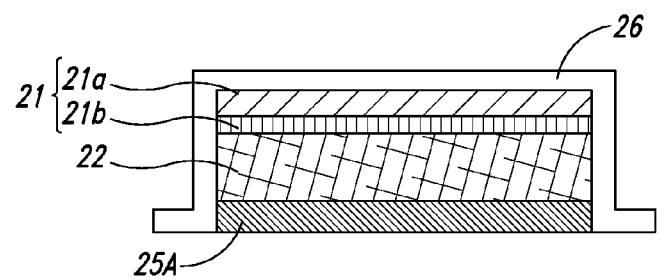

FIGS. 5A and 5B are explanatory sectional views showing the constitutions of active electrode assemblies 10J and 10K according to still another aspect each of which can be used as the active electrode assembly 10 of the iontophoresis device X.

The active electrode assembly 10J comprises the electrode 11 having the conductive base material 11a connected to the electric supply line 31 and the doping layer 11b formed on one surface of the base material 11a.

In the active electrode assembly 10J, the doping layer 11b is doped with active agent ions, and then an electrical potential or positive voltage is applied to the electrode 11 in a state where the doping layer 11b is brought into contact a biological interface of a subject (without or with an intervening transfer medium such as a gel or cream), whereby the active agent ions with which the doping layer 11b is doped is administered to the subject.

Energization from the doping layer 11b to a biological interface of the subject is caused by the movement of the active agent ion. Therefore, the generation of oxygen gas or chlorine gas, and the production of hydrogen ions or hypochlorous acid due to energization may be prevented or reduced.

In addition, the doping layer 11b doped with the active agent ion as a positive ion has a cation exchange function, so the transfer of a subject counter ion from the side of a biological interface to the doping layer 11b upon administration of an active agent is blocked and the active agent may be administered with high efficiency.

Referring to FIG. 5A and 5B, the active electrode assembly 10J has a simple structure comprising only the electrode 11. Therefore, the automation of the production of the active electrode assembly 10J and the mass production of the active electrode assembly 10J can be extremely easily performed, and the production cost of the active electrode assembly can be significantly reduced.

The doping layer 11b can be doped with the active agent ion through energization with the electrode 11 as a negative pole in a state where the doping layer 11b is immersed in an active agent solution containing an appropriate concentration of active agent ion. The doping may be performed at the stage of the production of the iontophoresis device X or the active electrode assembly 10J, or may be performed immediately before the administration of an active agent.

The active electrode assembly 10K comprises: the electrode 11 having the conductive base material 11a connected to the electric supply line 31 and the doping layer 11b formed on one surface of the base material 11a; and the cation exchange membrane 15 placed on the front surface side of the electrode 11.

In the active electrode assembly 10K, the cation exchange membrane 15 is, or the cation exchange membrane 15 and the doping layer 11b are, doped with active agent ions, and then a positive electrical potential or voltage is applied to the electrode 11 in a state where the cation exchange membrane 15 is brought into contact a biological interface of a subject (without or with an intervening transfer medium), whereby the active agent ions with which the cation exchange membrane 15 is, or the cation exchange membrane 15 and the doping layer 11b are doped is administered to the subject via the cation exchange membrane 15.

In the active electrode assembly 10K, energization from the electrode 11 to the cation exchange membrane 15 is caused by the transfer of the ions doping layer 11b to the cation exchange membrane. Therefore, the generation of oxygen gas or chlorine gas, and the production of hydrogen ions or hypochlorous acid due to energization may be prevented or reduced.

In addition, the active agent may be administered with high efficiency because the transfer of a subject counter ion from a subject to the doping layer 11b is blocked by the cation exchange membrane 15.

The active electrode assembly 10K has a simple structure comprising only the electrode 11 and the cation exchange membrane 15. Therefore, the automation of the production of the active electrode assembly 10K and the mass production of the active electrode assembly 10K can be extremely easily performed, and the production cost of the active electrode assembly can be significantly reduced.

In addition, the active electrode assembly 10K is structured in such a manner that the doping layer 11b does not directly contact a biological interface. Therefore, an active agent can be administered with substantially reduced possibility that harm or the like may be done to the health of a subject, even if the doping layer 11b is made using a substance not preferably brought into contact with the subject.

The cation exchange membrane 15, or the cation exchange membrane 15 and the doping layer 11b, can be doped with the active agent ion through energization with the electrode 11 as a negative pole in a state where the cation exchange membrane 15 is immersed in an active agent solution containing an appropriate concentration of active agent ion. The doping may be performed at the stage of the production of the iontophoresis device X or the active electrode assembly 10K, or may be performed immediately before the administration of an active agent.

The electrode 11 and the cation exchange membrane 15 may be joined and integrated with each other by means of an approach such as thermocompression bonding, whereby energization property between them and the handleability of them can be improved.

FIGS. 6A to 6D are explanatory sectional views showing the constitutions of counter electrode assemblies 20A and 20D each of which can be used as the counter electrode assembly 20 of the iontophoresis device X.

The counter electrode assembly 20A comprises an electrode 21 having a conductive base material 21a connected to the electric supply line 32 and a doping layer 21b formed on the base material 21a.

In the counter electrode assembly 20A, when a negative electrical potential or voltage is applied to the electrode 21 in a state where the doping layer 21b is brought into contact with a subject (without or with an intervening transfer medium), energization is caused by the transfer of positive ions from a biological interface of the subject to the doping layer 21b such that the layer is doped with the ion. Therefore, the generation of hydrogen gas or the production of a hydroxide ion upon energization may be prevented or reduced.

When a layer doped with a negative ion in advance is used as the doping layer 21b of the counter electrode assembly 20A, energization is caused by the transfer of negative ions to a biological interface of a subject and the transfer of positive ions from a biological interface of the subject to the doping layer 21b. Even in this case, the generation of hydrogen gas or the production of a hydroxide ion may be prevented or reduced.

The counter electrode assembly 20A has a similar configuration as that of the active electrode assembly 101, so the counter electrode assembly 20A and the active electrode assembly 10J can be produced by means of the same process. As a result, the production process of an iontophoresis device can be greatly simplified. In addition, the automation of the production of the iontophoresis device and the mass production of the iontophoresis device can be easily performed, and the production cost of the iontophoresis device can be significantly reduced.

The counter electrode assembly 20B comprises the electrode 21 identical to that of the counter electrode assembly 20A and a cation exchange membrane 25C placed on the front surface side of the doping layer 21b.

In the counter electrode assembly 20B, energization is caused by the transfer of positive ions from a biological interface of a subject to the doping layer 21b via the cation exchange membrane 25C such that the layer is doped with the ion. Therefore, the generation of hydrogen gas or the production of hydroxide ion upon energization may be prevented or reduced.

In addition, the counter electrode assembly 20B is structured in such a manner that the doping layer 21b does not directly contact a biological interface. Therefore, an active agent can be safely administered even when the doping layer 21b made of a substance which is not preferably brought into contact with a subject is used.

The electrode 21 and the cation exchange membrane 25C can be joined and integrated with each other by means of an approach such as thermocompression bonding. This action can improve energization property between them and the handleability of them.

The counter electrode assembly 20B has a similar configuration as that of the active electrode assembly 10K, so the counter electrode assembly 20B and the active electrode assembly 10K can be produced by means of the same process. As a result, the production process of an iontophoresis device can be significantly simplified. In addition, the automation of the production of the iontophoresis device and the mass production of the iontophoresis device can be easily performed, and the production cost of the iontophoresis device can be significantly reduced.

The counter electrode assembly 20C comprises: the electrode 21 having the conductive base material 21a connected to the electric supply line 32 and the doping layer 21b formed on the base material 21a and doped with a negative ion; and an anion exchange membrane 25A placed on the front surface side of the doping layer 21b.

In the counter electrode assembly 20C, when a negative electrical potential or voltage is applied to the electrode 21 in a state where the anion exchange membrane 25A is brought into contact with a subject (without or with an intervening transfer medium), a negative ion with which the doping layer 21b is doped transfers to the anion exchange membrane 25A, and the negative ion additionally transfers to the subject, or a counter ion bound to an ion exchange group in the anion exchange membrane 25A and substituted by the negative ion transfers to the subject, whereby energization occurs. Therefore, the generation of hydrogen gas or the production of a hydroxide ion upon energization may be prevented.

The electrode 21 and the anion exchange membrane 25A can be joined and integrated with each other by means of an approach such as thermocompression bonding. This action can improve energization property between them and the handleability of them.

The counter electrode assembly 20D comprises: the electrode 21 identical to that of the counter electrode assembly 20A; an electrolyte solution reservoir 22 holding an electrolyte solution in contact with the doping layer 21b; and the anion exchange membrane 25A placed on the front surface side of the electrolyte solution reservoir 22.

In the counter electrode assembly 20D, when a negative electrical potential or voltage is applied to the electrode 21 in a state where the anion exchange membrane 25A is brought into contact with a subject (without or with an intervening transfer medium), energization is caused by the transfer of positive ions in the electrolyte solution reservoir 22 to the doping layer 21b such that the layer is doped with the ion. Therefore, the generation of hydrogen gas or the production of a hydroxide ion upon energization may be suppressed.

Energization between the electrolyte solution reservoir 22 and a biological interface of the subject is caused by the transfer of negative ions in the electrolyte solution reservoir 22 to a biological interface of the subject via the anion exchange membrane 25A.

Figure 7A:
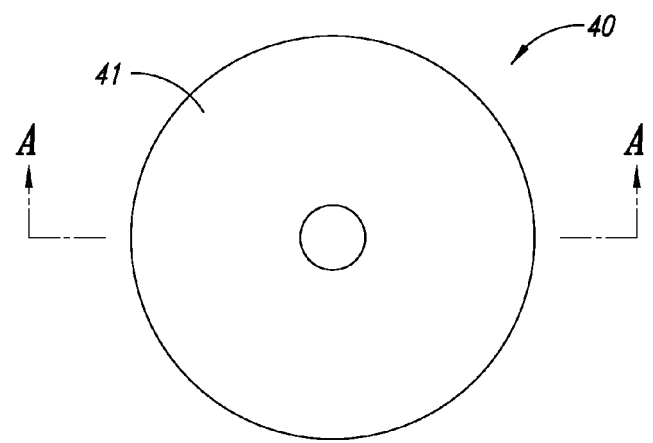
FIG. 7A is a plan view of an electrode to be used for an iontophoresis device according to an embodiment of the present invention.
Figure 7B:
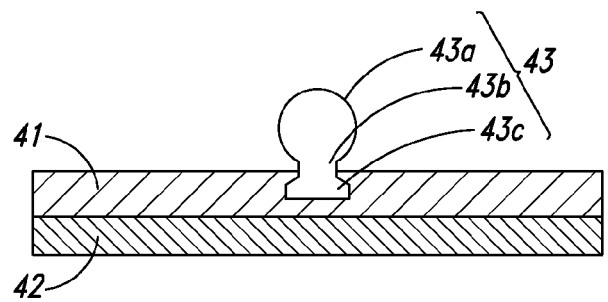
FIG. 7B is a sectional view taken along the line A-A of FIG. 7A.

FIG. 7A is a plan view of an electrode 40 to be particularly preferably used as the electrode 11 of each of the active electrode assemblies 10A to 10K or as the electrode 21 of each of the counter electrode assemblies 20A to 20D, and FIG. 7B is a sectional view taken along the line A-A of FIG. 7A.

Reference numeral 41 denotes a conductive base material comprising a carbon fiber, and a doping layer 42 made of a conductive polymer or the like is formed on one surface of the base material 41. A terminal member 43 comprising a male fitting portion 43a, a body portion 43b, and a joining portion 43c is attached to the other surface of the base material 41.

The terminal member 43 is obtained by curing a composition in a die placed on the base material 41. The composition may be prepared by blending a polymer matrix such as silicon rubber with graphite, black lead, carbon black, or a carbon filler such as fine powder of glass-like carbon or a short fiber obtained by cutting a carbon fiber, through heating and vulcanization. The composition is hardened in a state where it is impregnated into a carbon fiber constituting the base material 41, whereby the base material 41 and the terminal member 43 are integrated with each other at the joining portion 43c.

The electrode 40 enables energization from the doping layer 42 at a uniform current density because a carbon fiber has high conductivity and high flexibility. As a result, the active electrode assemblies 10A to 10K and the counter electrode assemblies 20A to 20D each having enough flexibility to follow the irregularities of a biological interface of a subject or the movement of the subject can be realized.

In addition, connection from the electric power source 30 to the electric supply lines 31 and 32 can be performed by means of a connector having a female fitting portion that fits into the male fitting portion 43a. Even when a metallic material is used for the female fitting portion, the metal of the connector is prevented from eluting and transferring to a subject because the male fitting portion 43a is separated from the base material 41 by the body portion 43b.

Figure 7C:
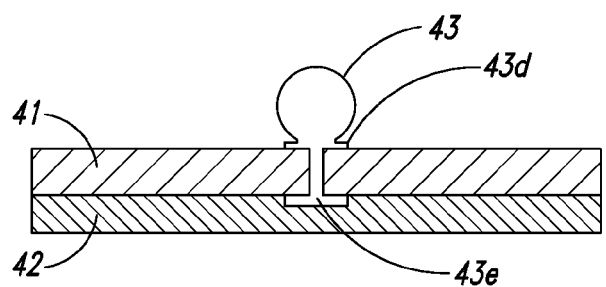
FIG. 7C is a sectional view showing a modification of FIG. 7B.

The terminal member 43 may be attached to the base material 41 by means of a variety of methods. For example, as shown in FIG. 7C, the attachment can be performed by: forming engaging portions 43d and 43e on the terminal member 43; and inserting the engaging portion 43e into a small pore arranged on the base material 41.

Figure 8A:
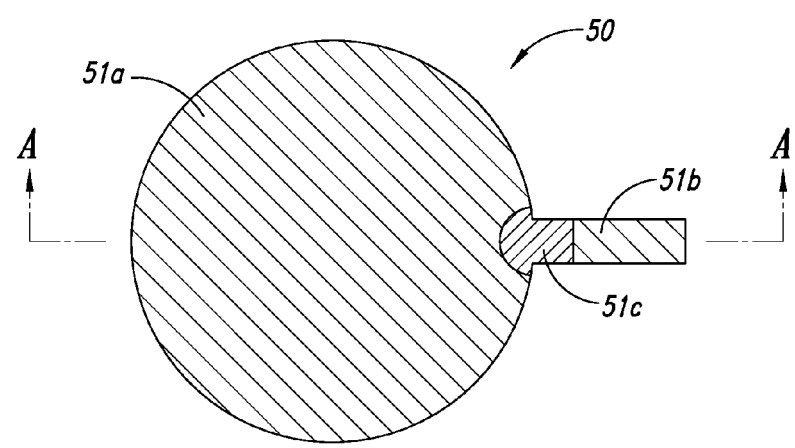
FIG. 8A is a plan view of an electrode according to another aspect to be used for an iontophoresis device according to an embodiment of the present invention.
Figure 8B:
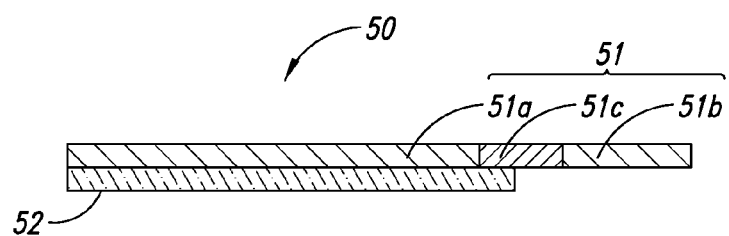
FIG. 8B is a sectional view taken along the line A-A of FIG. 8A.

FIG. 8A is a plan view of an electrode 50 according to another aspect to be particularly preferably used as the electrode 11 of each of the active electrode assemblies 10A to 10K or as the electrode 21 of each of the counter electrode assemblies 20A to 20D, and FIG. 8B is a sectional view taken along the line A-A of FIG. 8A.

Reference numeral 51 denotes a base material comprising a carbon fiber having a circular conductive sheet portion 51a and an elongated extension portion 51b extending from the conductive sheet portion 51a. A doping layer 52 is formed on one surface of the conductive sheet portion 51a.

The electrode 50 enables energization from the doping layer 52 at a uniform current density similar to the case of the electrode 40. As a result, the active electrode assemblies 10A to 10K and the counter electrode assemblies 20A to 20D each having enough flexibility to follow the irregularities of a biological interface of a subject or the movement of the subject can be realized.

Figure 8C:
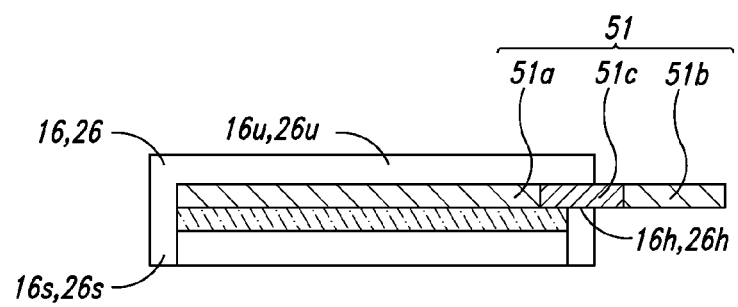
FIG. 8C is a sectional view showing a state where the electrode is housed in a container.

Referring to FIG. 8C, the electrode 50 may be used in combination with the container 16/26 having an opening 16h/26h formed on the outer peripheral wall 16s/26s or the upper wall 16u/26u, and may be housed in the container 16/26 in a state where the extension portion 51b is led from the opening 16h/26h.

Connection from the electric power source 30 to the electric supply lines 31 and 32 can be made at the extension portion 51b by means of a connector such as an alligator clip attached to the tip of each of the electric supply lines 31 and 32.

A member having a high water content such as the electrolyte solution reservoir 12 or 22, or the active agent solution reservoir 14, similar the active electrode assemblies 10A to 10E and the counter electrode assembly 20D, a water-repellent portion 51c impregnated with a fluorine base resin, a silicone base resin, a silane base resin, or the like used to provide water repellency may be arranged at the extension portion 51b placed at the opening 16h or 26h. As a result, water can be prevented from leaking from an active electrode assembly or a counter electrode assembly. Alternatively, when a metallic member is used for the connector such as an alligator clip, a metal ion eluted from the member can be prevented from penetrating into an active electrode assembly or a counter electrode assembly.

Each of the base materials 41 and 51 of the electrodes 40 and 50 can achieve an effect similar to that described above even when each of the materials is formed of carbon fiber paper. The carbon fiber or carbon fiber paper of the base material 41 or 51 is impregnated with a soft polymer such as silicon rubber or thermoplastic polyurethane, whereby a reduction in quality of an electrode due to the failing of a carbon fiber can be prevented, and the handleability of the electrode 40 or 50 can be improved.

While several embodiments have been described, the present invention is not limited to those embodiments, and can be variously altered within the scope of claims.

For example, the specific shape and dimensions of an electrode assembly, an electrode, or the like are shown merely as examples in each embodiment. The claims are not limited to the shapes, dimensions, and the like shown in the embodiments.

In addition, in each of the above embodiments, a description has been provided for a case where a conductive base material with a doping layer formed thereon is used as an electrode. However, the base material need not necessarily be conductive, and an electrode can be formed by only using a doping layer without the use of a base material.

Figure 9:
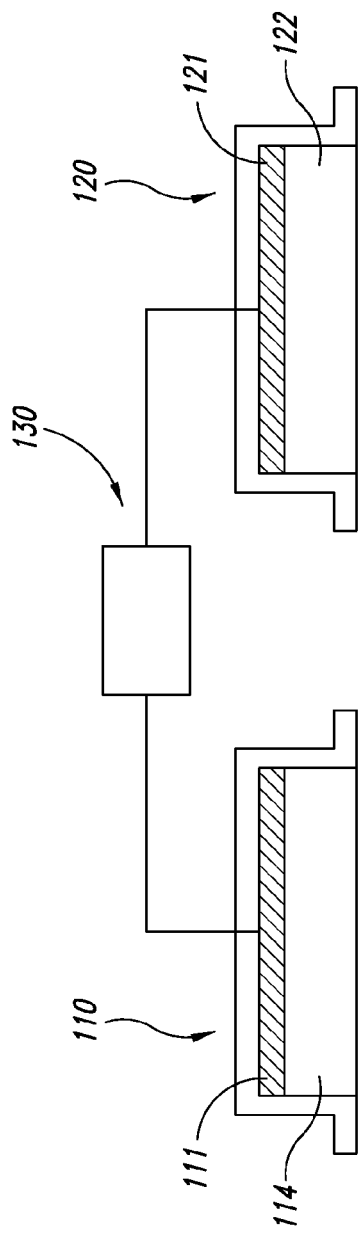
FIG. 9 is an explanatory view showing the constitution of a conventional iontophoresis device.
Figure 10:
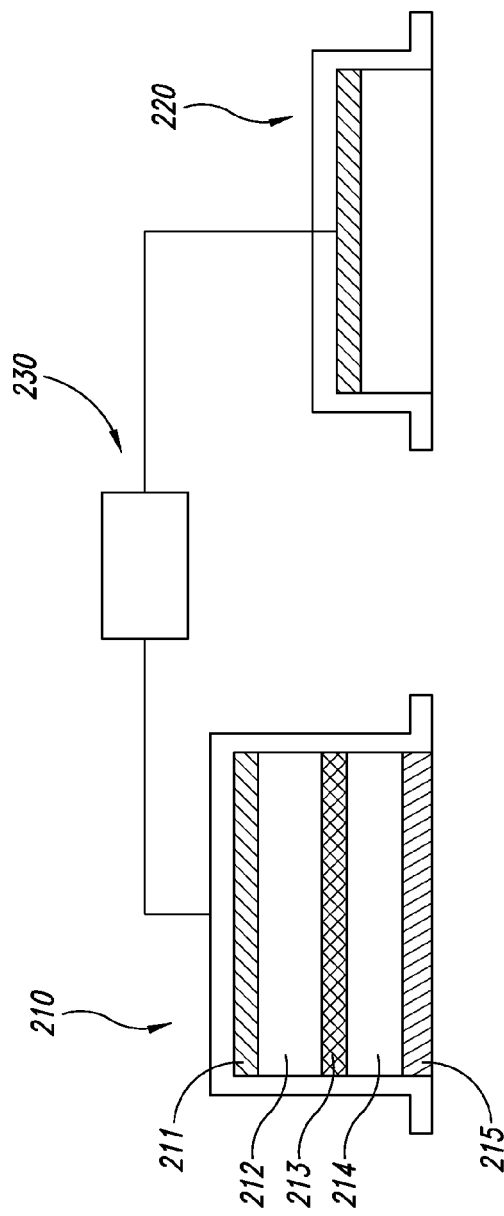
FIG. 10 is an explanatory view showing the constitution of another conventional iontophoresis device.

The iontophoresis device can be configured by combining one or more of the active electrode assemblies 10A to 10K and one or more of the counter electrode assemblies 20A to 20D. In addition, the iontophoresis device can be constituted by combining one or more of the active electrode assemblies 10A to 10K and the counter electrode assembly 120 or 210 shown in FIG. 9 or 10, or by combining one or more of the counter electrode assemblies 20A to 20D and the active electrode assembly 110 or 210 shown in FIG. 9 or 10.

Alternatively, an active agent can be administered as follows. While any one of the active electrode assemblies 10A to 10K is used, the iontophoresis device itself is provided with no counter electrode assembly, and, for example, an electrical potential or voltage is applied to the active electrode assembly in a state where the active electrode assembly is brought into contact a biological interface of a subject and a part of the subject is brought into contact with a member to serve as the ground. The basic effect, that is, the prevention of: the generation of oxygen gas, hydrogen gas, chlorine gas, or the like; or the production of hydrogen ions, hydroxide ions, or hypochlorous acid in an active electrode assembly upon energization may be achieved. Therefore, such iontophoresis device is also included in the scope of the disclosure.

Furthermore, in each of the above embodiments, description has been given of cases where the active electrode assembly, the counter electrode assembly, and the electric power source are configured separately. It is also possible that those elements are incorporated in a single casing or an entire device incorporating them is formed in a sheet shape or a patch shape, whereby the handleability thereof is enhanced. Such iontophoresis devices are also included in the scope of the disclosure.

The above description of illustrated embodiments, including what is described in the Abstract, is not intended to be exhaustive or to limit the embodiments to the precise forms disclosed. Although specific embodiments and examples are described herein for illustrative purposes, various equivalent modifications can be made without departing from the spirit and scope of the disclosure, as will be recognized by those skilled in the relevant art. The teachings provided herein of the various embodiments can be applied to other problem-solving systems devices, and methods, not necessarily the exemplary problem-solving systems devices, and methods generally described above.

For instance, the foregoing detailed description has set forth various embodiments of the systems, devices, and/or methods via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms taught herein are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety Aspects of the embodiments can be modified, if necessary, to employ systems, circuits, and concepts of the various patents, applications, and publications to provide yet further embodiments.

These and other changes can be made to the embodiments in light of the above-detailed description. In general, in the following claims, the terms used should not be construed to limit the invention to the specific embodiments disclosed in the specification and the claims, but should be construed to include all possible embodiments along with the full scope of equivalents to which such claims are entitled. Accordingly, the scope of the invention shall only be construed and defined by the scope of the appended claims.

What is claimed is:

1. An iontophoresis device, comprising:
    at least one electrode assembly, the electrode assembly including:
        active agent ions; and
        an electrode having a doping layer made of a material effecting an electrochemical reaction due to doping or de-doping of ions to administer at least some of the active agent ions to a subject.

2. The iontophoresis device according to claim 1 wherein the electrode assembly further comprises an active agent solution reservoir holding an active agent solution containing active agent ions of a first polarity, the active agent solution reservoir being located on a front surface side of the doping layer.

3. The iontophoresis device according to claim 1 wherein the electrode assembly further comprises:
    an electrolyte solution reservoir holding an electrolyte solution, the electrolyte solution reservoir being placed on a front surface side of the doping layer; and
    a first ion exchange membrane of the first polarity that is placed on a front surface side of the electrolyte solution reservoir and that is doped with active agent ions of a first polarity.

4. The iontophoresis device according to claim 1 wherein:
    the electrode assembly further comprises a first ion exchange membrane of a first polarity that is placed on a front surface side of the doping layer and that is doped with active agent ions of the first polarity; and
    the doping layer is doped with an ion of the first polarity.

5. The iontophoresis device according to claim 1 wherein the doping layer is doped with active agent ions of a first polarity.

6. The iontophoresis device according to claim 1 wherein the electrode assembly further comprises a first ion exchange membrane of a first polarity placed on a front surface side of the doping layer.

7. The iontophoresis device according to claim 1 wherein the doping layer contains a conductive polymer.

8. The iontophoresis device according to claim 5 wherein the electrode assembly further comprises an active agent solution reservoir holding an active agent solution containing active agent ions of the first polarity, the active agent solution reservoir being located on a front surface side of the doping layer.

9. The iontophoresis device according to claim 7 wherein the electrode assembly further comprises:
    an electrolyte solution reservoir holding an electrolyte solution, the electrolyte solution reservoir being placed on a front surface side of the doping layer; and
    a first ion exchange membrane of a first polarity that is placed on a front surface side of the electrolyte solution reservoir and that is doped with active agent ions of the first polarity.

10. The iontophoresis device according to claim 7 wherein:
    the electrode assembly further comprises a first ion exchange membrane of a first polarity that is placed on a front surface side of the doping layer and that is doped with active agent ions of the first polarity; and
    the doping layer is doped with an ion of the first polarity.

11. The iontophoresis device according to claim 7 wherein the doping layer is doped with active agent ions of a first polarity.

12. The iontophoresis device according to claim 7 wherein the electrode assembly further comprises a first ion exchange membrane of a first polarity placed on a front surface side of the doping layer.

13. The iontophoresis device according to claim 7 wherein the conductive polymer comprises at least one of polyaniline, polypyrrole, polythiophene or polyacetylene, or a derivative thereof.

14. The iontophoresis device according to claim 13 wherein the electrode assembly further comprises an active agent solution reservoir holding an active agent solution containing active agent ions of a first polarity, the active agent solution reservoir being located on a front surface side of the doping layer.

15. The iontophoresis device according to claim 14 wherein the electrode assembly further includes a first ion exchange membrane of the first polarity located on a front surface side of the active agent solution reservoir.

16. The iontophoresis device according to claim 15 wherein:
    the electrode assembly further comprises a second ion exchange membrane of a second polarity placed on the front surface side of the doping layer; and
    the active agent solution reservoir is placed on a front surface side of the second ion exchange membrane.

17. The iontophoresis device according to any one of claim 13 wherein the electrode assembly further comprises:
    an electrolyte solution reservoir holding an electrolyte solution, the electrolyte solution reservoir being placed on a front surface side of the doping layer; and
    a first ion exchange membrane of a first polarity that is placed on a front surface side of the electrolyte solution reservoir and that is doped with active agent ions of the first polarity.

18. The iontophoresis device according to claim 17 wherein:
the electrode assembly further comprises a second ion exchange membrane of a second polarity placed on the front surface side of the electrolyte solution reservoir; and
the first ion exchange membrane is placed on a front surface side of the second ion exchange membrane.

19. The iontophoresis device according to claim 17 wherein:
the electrode assembly further comprises a second ion exchange membrane of a second polarity placed on the front surface side of the doping layer; and
the electrolyte solution reservoir is placed on a front surface side of the second ion exchange membrane.

20. The iontophoresis device according to claim 13 wherein:
the electrode assembly further comprises a first ion exchange membrane of a first polarity that is placed on a front surface side of the doping layer and that is doped with active agent ions of the first polarity; and
the doping layer is doped with an ion of the first polarity.

21. The iontophoresis device according to claim 20 wherein:
the electrode assembly further comprises a second ion exchange membrane of a second polarity placed on a front surface side of the doping layer; and
the first ion exchange membrane is placed on a front surface side of the second ion exchange membrane.

22. The iontophoresis device according to claim 13 wherein the doping layer is doped with active agent ions of a first polarity.

23. The iontophoresis device according to claim 13 wherein the electrode assembly further comprises a first ion exchange membrane of a first polarity placed on a front surface side of the doping layer.

24. An iontophoresis device comprising:
an active electrode assembly holding active agent ions of a first polarity to be administered to a subject; and
a counter electrode assembly as a counter electrode of the active electrode assembly, the counter electrode assembly comprising an electrode that includes a doping layer made of a material effecting an electrochemical reaction owing to doping or de-doping of ions to administer at least some of the active agent ions to the subject.

25. The iontophoresis device according to claim 24 wherein the counter electrode assembly further comprises a third ion exchange membrane of the first polarity placed on a front surface side of the doping layer.

26. The iontophoresis device according to claim 24 wherein:
the counter electrode assembly further comprises a third ion exchange membrane of a second polarity that is placed on the front surface side of the doping layer; and
the doping layer is doped with an ion of the second polarity.

27. The iontophoresis device according to claim 26 wherein:
the electrode further comprises a conductive base material; and
the doping layer is stacked on the conductive base material.

28. The iontophoresis device according to claim 27 wherein the conductive base material comprises a conductive sheet made of a carbon fiber or carbon fiber paper.

29. The iontophoresis device according to claim 28 wherein the electrode further comprises a terminal member with carbon mixed in a polymer matrix, the terminal member being attached to the conductive sheet.

30. The iontophoresis device according to claim 28 wherein the electrode further comprises an extension portion that is formed integrally with the conductive sheet and that is made of a carbon fiber or carbon fiber paper.

* * * * *